United States Patent
Bianco et al.

(10) Patent No.: US 10,851,419 B2
(45) Date of Patent: Dec. 1, 2020

(54) MICROGLIA MICROVESICLES CONTAINED MICRORNA-BASED METHODS FOR THE DIAGNOSIS, PROGNOSIS AND TREATMENT MONITORING OF NEUROLOGICAL, NEURODEGENERATIVE AND INFLAMMATION-BASED DISEASES

(71) Applicant: BRAINDTECH S.P.A., Milan (IT)

(72) Inventors: Fabio Bianco, Milan (IT); Noemi Tonna, Milan (IT)

(73) Assignee: BRAINDTECH S.P.A., Milan (IT)

( * ) Notice: Subject to any disclaimer, the term of this patent is extended or adjusted under 35 U.S.C. 154(b) by 0 days.

(21) Appl. No.: 15/777,310

(22) PCT Filed: Nov. 18, 2016

(86) PCT No.: PCT/EP2016/078190
§ 371 (c)(1),
(2) Date: May 18, 2018

(87) PCT Pub. No.: WO2017/085287
PCT Pub. Date: May 26, 2017

(65) Prior Publication Data
US 2019/0249250 A1    Aug. 15, 2019

(30) Foreign Application Priority Data
Nov. 20, 2015   (IT) .................. 102015000074820

(51) Int. Cl.
*A61K 48/00* (2006.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/158* (2013.01); *C12Q 2600/178* (2013.01)

(58) Field of Classification Search
CPC ..................... C12N 15/113; A61K 31/713
See application file for complete search history.

(56) References Cited

FOREIGN PATENT DOCUMENTS

| EP | 2733219 A1 | 5/2014 | |
|---|---|---|---|
| WO | 2009036236 A1 | 3/2009 | |
| WO | WO 2011/057003 A2 * | 5/2011 | ........... C12N 15/113 |
| WO | 2011107962 A1 | 9/2011 | |
| WO | 2014075822 A1 | 5/2014 | |

OTHER PUBLICATIONS

Mattick et al. (Human Molecular Genetics, 2005, vol. 14, review issue 1, R121-R132).*
Cheng et al., "Prognostic serum miRNA biomarkers associated with Alzheimer's disease shows concordance with neuropsychological and neuroimaging assessment", Molecular Psychiatry, (2015), vol. 20, pp. 1188-1196.
Gui et al., "Altered microRNA profiles in cerebrospinal fluid exosome in Parkinson disease and Alzheimer disease", Oncotarget, (2015), vol. 6, No. 35, pp. 37043-37053.
Lugli et al., "Plasma Exosomal miRNAs in Persons with and without Alzheimer Disease: Altered Expression and Prospects for Biomarkers", PLoS ONE, (2015), vol. 10, pp. 1-18.
Porro et al., "Microvesicles in the brain: Biomarker, messenger or mediator?", Journal of Neuroimmunology, (2015), vol. 288, pp. 70-78.
PCT International Preliminary Report on Patentability, Application No. PCT/EP2016/078190, dated May 22, 2018.

* cited by examiner

*Primary Examiner* — Amy H Bowman
(74) *Attorney, Agent, or Firm* — MacMillan, Sobanski & Todd, LLC

(57) ABSTRACT

The present invention describes a method for the in vitro diagnosis, prognosis and/or treatment monitoring of neurodegenerative, neurological and inflammation-based diseases, wherein the method comprises the steps: a) isolating microglial microvesicles (MVs) from biological fluids obtained from an individual; b) collecting the microRNA (miRNA) contained into said MVs; c) determining the expression profile of a predetermined set of miRNA; d) comparing said expression profile to one or several reference expression profiles, wherein the comparison of said determined expression profile to said one or several reference expression profiles allows for the diagnosis, prognosis and/ or treatment monitoring of the disease.

2 Claims, No Drawings
Specification includes a Sequence Listing.

SEQUENCE LISTING

```
<160> NUMBER OF SEQ ID NOS: 246

<210> SEQ ID NO 1
<211> LENGTH: 24
<212> TYPE: RNA
<213> ORGANISM: Mus musculus

<400> SEQUENCE: 1
ucccugagac ccuuuaaccu guga                                          24

<210> SEQ ID NO 2
<211> LENGTH: 22
<212> TYPE: RNA
<213> ORGANISM: Mus musculus

<400> SEQUENCE: 2
uaugcaaggg caagcucucu uc                                            22

<210> SEQ ID NO 3
<211> LENGTH: 23
<212> TYPE: RNA
<213> ORGANISM: Mus musculus

<400> SEQUENCE: 3
gcaaagcaca gggccugcag aga                                           23

<210> SEQ ID NO 4
<211> LENGTH: 22
<212> TYPE: RNA
<213> ORGANISM: Mus musculus

<400> SEQUENCE: 4
uauacaugag agcauacaua ga                                            22

<210> SEQ ID NO 5
<211> LENGTH: 22
<212> TYPE: RNA
<213> ORGANISM: Mus musculus

<400> SEQUENCE: 5
aauccuuugu cccuggguga aa                                            22
```

-continued

```
<210> SEQ ID NO 6
<211> LENGTH: 22
<212> TYPE: RNA
<213> ORGANISM: Mus musculus

<400> SEQUENCE: 6
ugagaacuga auuccauggg uu                                               22

<210> SEQ ID NO 7
<211> LENGTH: 23
<212> TYPE: RNA
<213> ORGANISM: Mus musculus

<400> SEQUENCE: 7
gugccuacug agcugauauc agu                                              23

<210> SEQ ID NO 8
<211> LENGTH: 23
<212> TYPE: RNA
<213> ORGANISM: Mus musculus

<400> SEQUENCE: 8
caccaccucc ccugcaaacg ucc                                              23

<210> SEQ ID NO 9
<211> LENGTH: 22
<212> TYPE: RNA
<213> ORGANISM: Mus musculus

<400> SEQUENCE: 9
ugcggggcua gggcuaacag ca                                               22

<210> SEQ ID NO 10
<211> LENGTH: 23
<212> TYPE: RNA
<213> ORGANISM: Mus musculus

<400> SEQUENCE: 10
aggaagcccu ggaggggcug gag                                              23

<210> SEQ ID NO 11
<211> LENGTH: 22
<212> TYPE: RNA
<213> ORGANISM: Mus musculus

<400> SEQUENCE: 11
ugugacuggu ugaccagagg gg                                               22

<210> SEQ ID NO 12
<211> LENGTH: 20
<212> TYPE: RNA
<213> ORGANISM: Mus musculus

<400> SEQUENCE: 12
guagaggaga uggcgcaggg                                                  20

<210> SEQ ID NO 13
<211> LENGTH: 21
<212> TYPE: RNA
<213> ORGANISM: Mus musculus

<400> SEQUENCE: 13
ggguuccugg caugcugauu u                                                21
```

```
<210> SEQ ID NO 14
<211> LENGTH: 22
<212> TYPE: RNA
<213> ORGANISM: Mus musculus

<400> SEQUENCE: 14
auaguugugu guggaugugu gu                                            22

<210> SEQ ID NO 15
<211> LENGTH: 23
<212> TYPE: RNA
<213> ORGANISM: Mus musculus

<400> SEQUENCE: 15
uagcaccauu ugaaaucagu guu                                           23

<210> SEQ ID NO 16
<211> LENGTH: 21
<212> TYPE: RNA
<213> ORGANISM: Mus musculus

<400> SEQUENCE: 16
uagcagcaca gaaauauugg c                                             21

<210> SEQ ID NO 17
<211> LENGTH: 21
<212> TYPE: RNA
<213> ORGANISM: Mus musculus

<400> SEQUENCE: 17
ucgaggagcu cacagucuag u                                             21

<210> SEQ ID NO 18
<211> LENGTH: 19
<212> TYPE: RNA
<213> ORGANISM: Mus musculus

<400> SEQUENCE: 18
acuuagcagg uuguauuau                                                19

<210> SEQ ID NO 19
<211> LENGTH: 24
<212> TYPE: RNA
<213> ORGANISM: Mus musculus

<400> SEQUENCE: 19
gcacagugau gaacucugag ggcu                                          24

<210> SEQ ID NO 20
<211> LENGTH: 22
<212> TYPE: RNA
<213> ORGANISM: Mus musculus

<400> SEQUENCE: 20
ccaguauuga cugugcugcu ga                                            22

<210> SEQ ID NO 21
<211> LENGTH: 22
<212> TYPE: RNA
<213> ORGANISM: Mus musculus

<400> SEQUENCE: 21
uugcaaugau gguauucuga gg                                            22
```

-continued

```
<210> SEQ ID NO 22
<211> LENGTH: 26
<212> TYPE: RNA
<213> ORGANISM: Mus musculus

<400> SEQUENCE: 22
ccaaagcauc gcgaaggccc acggcg                                          26

<210> SEQ ID NO 23
<211> LENGTH: 22
<212> TYPE: RNA
<213> ORGANISM: Mus musculus

<400> SEQUENCE: 23
gggguuccug gggaugggau uu                                              22

<210> SEQ ID NO 24
<211> LENGTH: 23
<212> TYPE: RNA
<213> ORGANISM: Mus musculus

<400> SEQUENCE: 24
agguugggau uugucgcaau gcu                                             23

<210> SEQ ID NO 25
<211> LENGTH: 22
<212> TYPE: RNA
<213> ORGANISM: Mus musculus

<400> SEQUENCE: 25
agaguugcgu cuggacgucc cg                                              22

<210> SEQ ID NO 26
<211> LENGTH: 21
<212> TYPE: RNA
<213> ORGANISM: Mus musculus

<400> SEQUENCE: 26
cggggccgua gcacugucug a                                               21

<210> SEQ ID NO 27
<211> LENGTH: 24
<212> TYPE: RNA
<213> ORGANISM: Mus musculus

<400> SEQUENCE: 27
cuauaccagg augucagcau aguu                                            24

<210> SEQ ID NO 28
<211> LENGTH: 22
<212> TYPE: RNA
<213> ORGANISM: Mus musculus

<400> SEQUENCE: 28
ugaacuauug caguagccuc cu                                              22

<210> SEQ ID NO 29
<211> LENGTH: 21
<212> TYPE: RNA
<213> ORGANISM: Mus musculus

<400> SEQUENCE: 29
```
uaaccuguug aacaacugaa c					21

<210> SEQ ID NO 30
<211> LENGTH: 22
<212> TYPE: RNA
<213> ORGANISM: Mus musculus

<400> SEQUENCE: 30
aacaauaucc uggugcugag ug					22

<210> SEQ ID NO 31
<211> LENGTH: 21
<212> TYPE: RNA
<213> ORGANISM: Mus musculus

<400> SEQUENCE: 31
ugguagacua uggaacguag g					21

<210> SEQ ID NO 32
<211> LENGTH: 23
<212> TYPE: RNA
<213> ORGANISM: Mus musculus

<400> SEQUENCE: 32
uuaaugcuaa uugugauagg ggu					23

<210> SEQ ID NO 33
<211> LENGTH: 22
<212> TYPE: RNA
<213> ORGANISM: Mus musculus

<400> SEQUENCE: 33
uuuugcgaug uguuccuaau au					22

<210> SEQ ID NO 34
<211> LENGTH: 22
<212> TYPE: RNA
<213> ORGANISM: Mus musculus

<400> SEQUENCE: 34
aacccguaga uccgaacuug ug					22

<210> SEQ ID NO 35
<211> LENGTH: 21
<212> TYPE: RNA
<213> ORGANISM: Mus musculus

<400> SEQUENCE: 35
ucagugcaug acagaacuug g					21

<210> SEQ ID NO 36
<211> LENGTH: 21
<212> TYPE: RNA
<213> ORGANISM: Mus musculus

<400> SEQUENCE: 36
agcuacaucu ggcuacuggg u					21

<210> SEQ ID NO 37
<211> LENGTH: 22
<212> TYPE: RNA
<213> ORGANISM: Homo sapiens

<400> SEQUENCE: 37

```
ugagguagga gguuguauag uu                                        22

<210> SEQ ID NO 38
<211> LENGTH: 23
<212> TYPE: RNA
<213> ORGANISM: Homo sapiens

<400> SEQUENCE: 38
uaaggugcau cuagcugu uag                                         23

<210> SEQ ID NO 39
<211> LENGTH: 22
<212> TYPE: RNA
<213> ORGANISM: Homo sapiens

<400> SEQUENCE: 39
uaguuuugca uaguugcacu ac                                        22

<210> SEQ ID NO 40
<211> LENGTH: 23
<212> TYPE: RNA
<213> ORGANISM: Mus musculus

<400> SEQUENCE: 40
uaguuuauca gacugauauu ucc                                       23

<210> SEQ ID NO 41
<211> LENGTH: 21
<212> TYPE: RNA
<213> ORGANISM: Homo sapiens

<400> SEQUENCE: 41
uucaaguaau ucaggauagg u                                         21

<210> SEQ ID NO 42
<211> LENGTH: 22
<212> TYPE: RNA
<213> ORGANISM: Homo sapiens

<400> SEQUENCE: 42
gcugguuuca uauggugguu ua                                        22

<210> SEQ ID NO 43
<211> LENGTH: 23
<212> TYPE: RNA
<213> ORGANISM: Homo sapiens

<400> SEQUENCE: 43
uguaaacauc cuacacucuc agc                                       23

<210> SEQ ID NO 44
<211> LENGTH: 22
<212> TYPE: RNA
<213> ORGANISM: Homo sapiens

<400> SEQUENCE: 44
aacccguaga uccgaacuug ug                                        22

<210> SEQ ID NO 45
<211> LENGTH: 22
<212> TYPE: RNA
<213> ORGANISM: Homo sapiens
```

-continued

```
<400> SEQUENCE: 45
gcucuuuuca cauugugcua cu                                              22

<210> SEQ ID NO 46
<211> LENGTH: 22
<212> TYPE: RNA
<213> ORGANISM: Homo sapiens

<400> SEQUENCE: 46
aacauucaac cugucgguga gu                                              22

<210> SEQ ID NO 47
<211> LENGTH: 22
<212> TYPE: RNA
<213> ORGANISM: Mus musculus

<400> SEQUENCE: 47
auguaugugu gcaugugcau gu                                              22

<210> SEQ ID NO 48
<211> LENGTH: 22
<212> TYPE: RNA
<213> ORGANISM: Homo sapiens

<400> SEQUENCE: 48
ucucugggcc ugugucuuag gc                                              22

<210> SEQ ID NO 49
<211> LENGTH: 22
<212> TYPE: RNA
<213> ORGANISM: Homo sapiens

<400> SEQUENCE: 49
aggggugcua ucugugauug ag                                              22

<210> SEQ ID NO 50
<211> LENGTH: 22
<212> TYPE: RNA
<213> ORGANISM: Homo sapiens

<400> SEQUENCE: 50
ucaggcucag uccccucccg au                                              22

<210> SEQ ID NO 51
<211> LENGTH: 22
<212> TYPE: RNA
<213> ORGANISM: Homo sapiens

<400> SEQUENCE: 51
aguuuugugu gcaugugcau gu                                              22

<210> SEQ ID NO 52
<211> LENGTH: 22
<212> TYPE: RNA
<213> ORGANISM: Homo sapiens

<400> SEQUENCE: 52
ugucuugugu gugcauguuc au                                              22

<210> SEQ ID NO 53
<211> LENGTH: 22
<212> TYPE: RNA
<213> ORGANISM: Homo sapiens
```

```
<400> SEQUENCE: 53
caacuagacu gugagcuucu ag                                             22

<210> SEQ ID NO 54
<211> LENGTH: 22
<212> TYPE: RNA
<213> ORGANISM: Homo sapiens

<400> SEQUENCE: 54
ugagaacuga auuccauagg cu                                             22

<210> SEQ ID NO 55
<211> LENGTH: 21
<212> TYPE: RNA
<213> ORGANISM: Homo sapiens

<400> SEQUENCE: 55
caucccuugc augguggagg g                                              21

<210> SEQ ID NO 56
<211> LENGTH: 23
<212> TYPE: RNA
<213> ORGANISM: Homo sapiens

<400> SEQUENCE: 56
ugucugcccg agugccugcc ucu                                            23

<210> SEQ ID NO 57
<211> LENGTH: 22
<212> TYPE: RNA
<213> ORGANISM: Mus musculus

<400> SEQUENCE: 57
uacgugugug ugcaugugca ug                                             22

<210> SEQ ID NO 58
<211> LENGTH: 25
<212> TYPE: RNA
<213> ORGANISM: Homo sapiens

<400> SEQUENCE: 58
aagggauucu gauguugguc acacu                                          25

<210> SEQ ID NO 59
<211> LENGTH: 22
<212> TYPE: RNA
<213> ORGANISM: Homo sapiens

<400> SEQUENCE: 59
agagaaaccc ugucucaaaa aa                                             22

<210> SEQ ID NO 60
<211> LENGTH: 21
<212> TYPE: RNA
<213> ORGANISM: Homo sapiens

<400> SEQUENCE: 60
cuccuucacc cgggcgguac c                                              21

<210> SEQ ID NO 61
<211> LENGTH: 21
<212> TYPE: RNA
```

<213> ORGANISM: Homo sapiens

<400> SEQUENCE: 61
cgacgagggc cggucggucg c                                              21

<210> SEQ ID NO 62
<211> LENGTH: 21
<212> TYPE: RNA
<213> ORGANISM: Homo sapiens

<400> SEQUENCE: 62
gugaggacug gggaggugga g                                              21

<210> SEQ ID NO 63
<211> LENGTH: 23
<212> TYPE: RNA
<213> ORGANISM: Homo sapiens

<400> SEQUENCE: 63
uacccuguag aaccgaauuu gug                                            23

<210> SEQ ID NO 64
<211> LENGTH: 22
<212> TYPE: RNA
<213> ORGANISM: Homo sapiens

<400> SEQUENCE: 64
aguucuucag uggcaagcuu ua                                             22

<210> SEQ ID NO 65
<211> LENGTH: 21
<212> TYPE: RNA
<213> ORGANISM: Homo sapiens

<400> SEQUENCE: 65
ggguuccugg caugcugauu u                                              21

<210> SEQ ID NO 66
<211> LENGTH: 22
<212> TYPE: RNA
<213> ORGANISM: Homo sapiens

<400> SEQUENCE: 66
aaccguggcu uucgauuguu ac                                             22

<210> SEQ ID NO 67
<211> LENGTH: 24
<212> TYPE: RNA
<213> ORGANISM: Homo sapiens

<400> SEQUENCE: 67
gaaguucugu uauacacuca ggcu                                           24

<210> SEQ ID NO 68
<211> LENGTH: 22
<212> TYPE: RNA
<213> ORGANISM: Homo sapiens

<400> SEQUENCE: 68
uagguuaucc guguugccuu cg                                             22

<210> SEQ ID NO 69
<211> LENGTH: 22

```
<212> TYPE: RNA
<213> ORGANISM: Homo sapiens

<400> SEQUENCE: 69
uauggcacug guagaauuca cu                                              22

<210> SEQ ID NO 70
<211> LENGTH: 22
<212> TYPE: RNA
<213> ORGANISM: Homo sapiens

<400> SEQUENCE: 70
cggcgucaug caggaguuga uu                                              22

<210> SEQ ID NO 71
<211> LENGTH: 23
<212> TYPE: RNA
<213> ORGANISM: Homo sapiens

<400> SEQUENCE: 71
aguuuugcag guuugcaucc agc                                             23

<210> SEQ ID NO 72
<211> LENGTH: 22
<212> TYPE: RNA
<213> ORGANISM: Homo sapiens

<400> SEQUENCE: 72
uguaaacauc cucgacugga ag                                              22

<210> SEQ ID NO 73
<211> LENGTH: 21
<212> TYPE: RNA
<213> ORGANISM: Homo sapiens

<400> SEQUENCE: 73
gugcauugua guugcauugc a                                               21

<210> SEQ ID NO 74
<211> LENGTH: 22
<212> TYPE: RNA
<213> ORGANISM: Homo sapiens

<400> SEQUENCE: 74
cacccguaga accgaccuug cg                                              22

<210> SEQ ID NO 75
<211> LENGTH: 23
<212> TYPE: RNA
<213> ORGANISM: Homo sapiens

<400> SEQUENCE: 75
ggauaucauc auauacugua agu                                             23

<210> SEQ ID NO 76
<211> LENGTH: 21
<212> TYPE: RNA
<213> ORGANISM: Mus musculus

<400> SEQUENCE: 76
cuagacugag gcuccuugag g                                               21

<210> SEQ ID NO 77
```

```
<211> LENGTH: 25
<212> TYPE: RNA
<213> ORGANISM: Homo sapiens

<400> SEQUENCE: 77
uuuggcaaug guagaacuca caccg                                          25

<210> SEQ ID NO 78
<211> LENGTH: 23
<212> TYPE: RNA
<213> ORGANISM: Homo sapiens

<400> SEQUENCE: 78
cguguauuug acaagcugag uug                                            23

<210> SEQ ID NO 79
<211> LENGTH: 22
<212> TYPE: RNA
<213> ORGANISM: Homo sapiens

<400> SEQUENCE: 79
uccgucucag uuacuuuaua gc                                             22

<210> SEQ ID NO 80
<211> LENGTH: 22
<212> TYPE: RNA
<213> ORGANISM: Homo sapiens

<400> SEQUENCE: 80
auauaauaca accugcuaag ug                                             22

<210> SEQ ID NO 81
<211> LENGTH: 23
<212> TYPE: RNA
<213> ORGANISM: Homo sapiens

<400> SEQUENCE: 81
ucuuggagua gaucaguggg cag                                            23

<210> SEQ ID NO 82
<211> LENGTH: 21
<212> TYPE: RNA
<213> ORGANISM: Homo sapiens

<400> SEQUENCE: 82
cgggaacguc gagacuggag c                                              21

<210> SEQ ID NO 83
<211> LENGTH: 22
<212> TYPE: RNA
<213> ORGANISM: Homo sapiens

<400> SEQUENCE: 83
ugagguagua gguuguauag uu                                             22

<210> SEQ ID NO 84
<211> LENGTH: 22
<212> TYPE: RNA
<213> ORGANISM: Homo sapiens

<400> SEQUENCE: 84
uguaaacauc cuacacucag cu                                             22
```

```
<210> SEQ ID NO 85
<211> LENGTH: 23
<212> TYPE: RNA
<213> ORGANISM: Homo sapiens

<400> SEQUENCE: 85
agcuucuuua cagugcugcc uug                                               23

<210> SEQ ID NO 86
<211> LENGTH: 23
<212> TYPE: RNA
<213> ORGANISM: Homo sapiens

<400> SEQUENCE: 86
agcuucuuua caguguugcc uug                                               23

<210> SEQ ID NO 87
<211> LENGTH: 21
<212> TYPE: RNA
<213> ORGANISM: Homo sapiens

<400> SEQUENCE: 87
cauaaaguag aaagcacuac u                                                 21

<210> SEQ ID NO 88
<211> LENGTH: 22
<212> TYPE: RNA
<213> ORGANISM: Homo sapiens

<400> SEQUENCE: 88
ugagaacuga auuccauggg uu                                                22

<210> SEQ ID NO 89
<211> LENGTH: 20
<212> TYPE: RNA
<213> ORGANISM: Homo sapiens

<400> SEQUENCE: 89
auaauacaac cugcuaagug                                                   20

<210> SEQ ID NO 90
<211> LENGTH: 22
<212> TYPE: RNA
<213> ORGANISM: Mus musculus

<400> SEQUENCE: 90
auuauuacuc acgguacgag uu                                                22

<210> SEQ ID NO 91
<211> LENGTH: 22
<212> TYPE: RNA
<213> ORGANISM: Homo sapiens

<400> SEQUENCE: 91
ugugacuggu ugaccagagg gg                                                22

<210> SEQ ID NO 92
<211> LENGTH: 22
<212> TYPE: RNA
<213> ORGANISM: Mus musculus

<400> SEQUENCE: 92
gccuucucuu cccgguucuu cc                                                22
```

```
<210> SEQ ID NO 93
<211> LENGTH: 22
<212> TYPE: RNA
<213> ORGANISM: Homo sapiens

<400> SEQUENCE: 93
ugagguagua gguuguauag uu                                        22

<210> SEQ ID NO 94
<211> LENGTH: 22
<212> TYPE: RNA
<213> ORGANISM: Homo sapiens

<400> SEQUENCE: 94
uggcaguguc uuagcugguu gu                                        22

<210> SEQ ID NO 95
<211> LENGTH: 24
<212> TYPE: RNA
<213> ORGANISM: Homo sapiens

<400> SEQUENCE: 95
agggacggga cguggugcag uguu                                      24

<210> SEQ ID NO 96
<211> LENGTH: 22
<212> TYPE: RNA
<213> ORGANISM: Homo sapiens

<400> SEQUENCE: 96
uucccuuugu cauccuuugc cu                                        22

<210> SEQ ID NO 97
<211> LENGTH: 22
<212> TYPE: RNA
<213> ORGANISM: Homo sapiens

<400> SEQUENCE: 97
ugagguagua gauuguauag uu                                        22

<210> SEQ ID NO 98
<211> LENGTH: 24
<212> TYPE: RNA
<213> ORGANISM: Homo sapiens

<400> SEQUENCE: 98
aguuuugcag auuugcaguu cagc                                      24

<210> SEQ ID NO 99
<211> LENGTH: 23
<212> TYPE: RNA
<213> ORGANISM: Homo sapiens

<400> SEQUENCE: 99
acggguauuc uuggguggau aau                                       23

<210> SEQ ID NO 100
<211> LENGTH: 23
<212> TYPE: RNA
<213> ORGANISM: Homo sapiens

<400> SEQUENCE: 100
uuaaugcuaa uugugauagg ggu                                       23
```

```
<210> SEQ ID NO 101
<211> LENGTH: 22
<212> TYPE: RNA
<213> ORGANISM: Homo sapiens

<400> SEQUENCE: 101
agauguccag ccacaauucu cg                                              22

<210> SEQ ID NO 102
<211> LENGTH: 22
<212> TYPE: RNA
<213> ORGANISM: Homo sapiens

<400> SEQUENCE: 102
aacaauaucc uggugcugag ug                                              22

<210> SEQ ID NO 103
<211> LENGTH: 22
<212> TYPE: RNA
<213> ORGANISM: Homo sapiens

<400> SEQUENCE: 103
guggauauuc cuucuauguu ua                                              22

<210> SEQ ID NO 104
<211> LENGTH: 21
<212> TYPE: RNA
<213> ORGANISM: Homo sapiens

<400> SEQUENCE: 104
ugguagacua uggaacguag g                                               21

<210> SEQ ID NO 105
<211> LENGTH: 22
<212> TYPE: RNA
<213> ORGANISM: Homo sapiens

<400> SEQUENCE: 105
aaaccguuac cauuacugag uu                                              22

<210> SEQ ID NO 106
<211> LENGTH: 22
<212> TYPE: RNA
<213> ORGANISM: Homo sapiens

<400> SEQUENCE: 106
agguuguccg uguugucuuc uc                                              22

<210> SEQ ID NO 107
<211> LENGTH: 23
<212> TYPE: RNA
<213> ORGANISM: Homo sapiens

<400> SEQUENCE: 107
caaagugcuu acagugcagg uag                                             23

<210> SEQ ID NO 108
<211> LENGTH: 23
<212> TYPE: RNA
<213> ORGANISM: Homo sapiens

<400> SEQUENCE: 108
```
uaaagugcuu auagugcagg uag                                           23

<210> SEQ ID NO 109
<211> LENGTH: 22
<212> TYPE: RNA
<213> ORGANISM: Homo sapiens

<400> SEQUENCE: 109
ugagguagua gguuguaugg uu                                            22

<210> SEQ ID NO 110
<211> LENGTH: 23
<212> TYPE: RNA
<213> ORGANISM: Homo sapiens

<400> SEQUENCE: 110
caaagugcuc auagugcagg uag                                           23

<210> SEQ ID NO 111
<211> LENGTH: 22
<212> TYPE: RNA
<213> ORGANISM: Homo sapiens

<400> SEQUENCE: 111
auuccuggaa auacuguucu ug                                            22

<210> SEQ ID NO 112
<211> LENGTH: 22
<212> TYPE: RNA
<213> ORGANISM: Homo sapiens

<400> SEQUENCE: 112
caaagaauuc uccuuuggg cu                                             22

<210> SEQ ID NO 113
<211> LENGTH: 22
<212> TYPE: RNA
<213> ORGANISM: Homo sapiens

<400> SEQUENCE: 113
uauucauuua cuccccagcc ua                                            22

<210> SEQ ID NO 114
<211> LENGTH: 20
<212> TYPE: RNA
<213> ORGANISM: Homo sapiens

<400> SEQUENCE: 114
aaacgccauu aucacacuaa                                               20

<210> SEQ ID NO 115
<211> LENGTH: 23
<212> TYPE: RNA
<213> ORGANISM: Homo sapiens

<400> SEQUENCE: 115
agguuacccg agcaacuuug cau                                           23

<210> SEQ ID NO 116
<211> LENGTH: 23
<212> TYPE: RNA
<213> ORGANISM: Homo sapiens

<400> SEQUENCE: 116
cccaguguuu agacuaccug uuc                                            23

<210> SEQ ID NO 117
<211> LENGTH: 26
<212> TYPE: RNA
<213> ORGANISM: Homo sapiens

<400> SEQUENCE: 117
accuggcaua caauguagau uucugu                                         26

<210> SEQ ID NO 118
<211> LENGTH: 21
<212> TYPE: RNA
<213> ORGANISM: Homo sapiens

<400> SEQUENCE: 118
agggcccccc cucaauccug u                                              21

<210> SEQ ID NO 119
<211> LENGTH: 22
<212> TYPE: RNA
<213> ORGANISM: mus musculus

<400> SEQUENCE: 119
agagguuuuc uggucucug uu                                              22

<210> SEQ ID NO 120
<211> LENGTH: 22
<212> TYPE: RNA
<213> ORGANISM: Homo sapiens

<400> SEQUENCE: 120
gaaguuguuc gugguggauu cg                                             22

<210> SEQ ID NO 121
<211> LENGTH: 22
<212> TYPE: RNA
<213> ORGANISM: Homo sapiens

<400> SEQUENCE: 121
ugaccgauuu cuccuggugu uc                                             22

<210> SEQ ID NO 122
<211> LENGTH: 21
<212> TYPE: RNA
<213> ORGANISM: Homo sapiens

<400> SEQUENCE: 122
cggggccgua gcacugucug a                                              21

<210> SEQ ID NO 123
<211> LENGTH: 23
<212> TYPE: RNA
<213> ORGANISM: Homo sapiens

<400> SEQUENCE: 123
agcugguguu gugaaucagg ccg                                            23

<210> SEQ ID NO 124
<211> LENGTH: 21
<212> TYPE: RNA
<213> ORGANISM: Homo sapiens

```
<400> SEQUENCE: 124
uugugcuuga ucuaaccaug u                                      21

<210> SEQ ID NO 125
<211> LENGTH: 21
<212> TYPE: RNA
<213> ORGANISM: Homo sapiens

<400> SEQUENCE: 125
ucaguagcca guguagaucc u                                      21

<210> SEQ ID NO 126
<211> LENGTH: 23
<212> TYPE: RNA
<213> ORGANISM: Homo sapiens

<400> SEQUENCE: 126
ugaucuagcc aaagccugac ugu                                    23

<210> SEQ ID NO 127
<211> LENGTH: 22
<212> TYPE: RNA
<213> ORGANISM: Mus musculus

<400> SEQUENCE: 127
ugaugugugu guacauguac au                                     22

<210> SEQ ID NO 128
<211> LENGTH: 22
<212> TYPE: RNA
<213> ORGANISM: Homo sapiens

<400> SEQUENCE: 128
cacagcuccc aucucagaac aa                                     22

<210> SEQ ID NO 129
<211> LENGTH: 23
<212> TYPE: RNA
<213> ORGANISM: Homo sapiens

<400> SEQUENCE: 129
gcuucuccug gcucuccucc cuc                                    23

<210> SEQ ID NO 130
<211> LENGTH: 23
<212> TYPE: RNA
<213> ORGANISM: Homo sapiens

<400> SEQUENCE: 130
uaaggugcau cuagugcaga uag                                    23

<210> SEQ ID NO 131
<211> LENGTH: 22
<212> TYPE: RNA
<213> ORGANISM: Homo sapiens

<400> SEQUENCE: 131
uugcauaugu aggauguccc au                                     22

<210> SEQ ID NO 132
<211> LENGTH: 22
<212> TYPE: RNA
<213> ORGANISM: Homo sapiens
```

```
<400> SEQUENCE: 132
ugaugugugu guacauguac au                                               22

<210> SEQ ID NO 133
<211> LENGTH: 22
<212> TYPE: RNA
<213> ORGANISM: Homo sapiens

<400> SEQUENCE: 133
uacacacaca cacacaagua aa                                               22

<210> SEQ ID NO 134
<211> LENGTH: 22
<212> TYPE: RNA
<213> ORGANISM: Homo sapiens

<400> SEQUENCE: 134
agagguagua gguugcauag uu                                               22

<210> SEQ ID NO 135
<211> LENGTH: 22
<212> TYPE: RNA
<213> ORGANISM: Homo sapiens

<400> SEQUENCE: 135
uguaaacauc cuugacugga ag                                               22

<210> SEQ ID NO 136
<211> LENGTH: 23
<212> TYPE: RNA
<213> ORGANISM: Homo sapiens

<400> SEQUENCE: 136
aggcagugua auuagcugau ugu                                              23

<210> SEQ ID NO 137
<211> LENGTH: 22
<212> TYPE: RNA
<213> ORGANISM: Homo sapiens

<400> SEQUENCE: 137
cuauacaacu uacuacuuuc cu                                               22

<210> SEQ ID NO 138
<211> LENGTH: 22
<212> TYPE: RNA
<213> ORGANISM: Homo sapiens

<400> SEQUENCE: 138
cguguucaca gcggaccuug au                                               22

<210> SEQ ID NO 139
<211> LENGTH: 23
<212> TYPE: RNA
<213> ORGANISM: Homo sapiens

<400> SEQUENCE: 139
aacauucaac gcugucggug agu                                              23

<210> SEQ ID NO 140
<211> LENGTH: 23
<212> TYPE: RNA
```

```
<213> ORGANISM: Homo sapiens

<400> SEQUENCE: 140
aacauucauu gcugucggug ggu                                           23

<210> SEQ ID NO 141
<211> LENGTH: 23
<212> TYPE: RNA
<213> ORGANISM: Homo sapiens

<400> SEQUENCE: 141
aacauucauu guugucggug ggu                                           23

<210> SEQ ID NO 142
<211> LENGTH: 22
<212> TYPE: RNA
<213> ORGANISM: Homo sapiens

<400> SEQUENCE: 142
uggagagaaa ggcaguuccu ga                                            22

<210> SEQ ID NO 143
<211> LENGTH: 22
<212> TYPE: RNA
<213> ORGANISM: Homo sapiens

<400> SEQUENCE: 143
aggcuacaac acaggacccg gg                                            22

<210> SEQ ID NO 144
<211> LENGTH: 22
<212> TYPE: RNA
<213> ORGANISM: Homo sapiens

<400> SEQUENCE: 144
ugauauguuu gauauauuag gu                                            22

<210> SEQ ID NO 145
<211> LENGTH: 23
<212> TYPE: RNA
<213> ORGANISM: Homo sapiens

<400> SEQUENCE: 145
caacggaauc ccaaaagcag cug                                           23

<210> SEQ ID NO 146
<211> LENGTH: 22
<212> TYPE: RNA
<213> ORGANISM: Homo sapiens

<400> SEQUENCE: 146
gcucugacuu uauugcacua cu                                            22

<210> SEQ ID NO 147
<211> LENGTH: 23
<212> TYPE: RNA
<213> ORGANISM: Homo sapiens

<400> SEQUENCE: 147
ccuaguaggu gcucaguaag ugu                                           23

<210> SEQ ID NO 148
<211> LENGTH: 22
```

<212> TYPE: RNA
<213> ORGANISM: Homo sapiens

<400> SEQUENCE: 148
cuagguaugg ucccagggau cc                                          22

<210> SEQ ID NO 149
<211> LENGTH: 22
<212> TYPE: RNA
<213> ORGANISM: Homo sapiens

<400> SEQUENCE: 149
gcugaccccu aguccagugc uu                                          22

<210> SEQ ID NO 150
<211> LENGTH: 22
<212> TYPE: RNA
<213> ORGANISM: Homo sapiens

<400> SEQUENCE: 150
uuaucagaau cuccaggggu ac                                          22

<210> SEQ ID NO 151
<211> LENGTH: 22
<212> TYPE: RNA
<213> ORGANISM: Homo sapiens

<400> SEQUENCE: 151
augguugacc auagaacaug cg                                          22

<210> SEQ ID NO 152
<211> LENGTH: 23
<212> TYPE: RNA
<213> ORGANISM: Homo sapiens

<400> SEQUENCE: 152
agcgagguug cccuuuguau auu                                         23

<210> SEQ ID NO 153
<211> LENGTH: 22
<212> TYPE: DNA
<213> ORGANISM: Homo sapiens

<400> SEQUENCE: 153
uuuugcgaug uguuccuaau au                                          22

<210> SEQ ID NO 154
<211> LENGTH: 22
<212> TYPE: RNA
<213> ORGANISM: Homo sapiens

<400> SEQUENCE: 154
ugagaacuga auuccauagg cu                                          22

<210> SEQ ID NO 155
<211> LENGTH: 24
<212> TYPE: RNA
<213> ORGANISM: Mus musculus

<400> SEQUENCE: 155
caccacagug ugguuuggac gugg                                        24

<210> SEQ ID NO 156

```
<211> LENGTH: 23
<212> TYPE: RNA
<213> ORGANISM: Homo sapiens

<400> SEQUENCE: 156
gggagccagg aaguauugau guu                                              23

<210> SEQ ID NO 157
<211> LENGTH: 23
<212> TYPE: RNA
<213> ORGANISM: Homo sapiens

<400> SEQUENCE: 157
gaaaucaagc uugggugaga ccu                                              23

<210> SEQ ID NO 158
<211> LENGTH: 21
<212> TYPE: RNA
<213> ORGANISM: Homo sapiens

<400> SEQUENCE: 158
uacucacaug guugcuaauc a                                                21

<210> SEQ ID NO 159
<211> LENGTH: 22
<212> TYPE: RNA
<213> ORGANISM: Homo sapiens

<400> SEQUENCE: 159
uauaccucag uuuuaucagg ug                                               22

<210> SEQ ID NO 160
<211> LENGTH: 24
<212> TYPE: RNA
<213> ORGANISM: Homo sapiens

<400> SEQUENCE: 160
cccaguuacc gcuuccgcua ccgc                                             24

<210> SEQ ID NO 161
<211> LENGTH: 22
<212> TYPE: RNA
<213> ORGANISM: Homo sapiens

<400> SEQUENCE: 161
uagcuuauca gacugauguu ga                                               22

<210> SEQ ID NO 162
<211> LENGTH: 22
<212> TYPE: RNA
<213> ORGANISM: Homo sapiens

<400> SEQUENCE: 162
gugccuacug agcugaaaca gu                                               22

<210> SEQ ID NO 163
<211> LENGTH: 22
<212> TYPE: RNA
<213> ORGANISM: Homo sapiens

<400> SEQUENCE: 163
agagcuuagc ugauugguga ac                                               22
```

```
<210> SEQ ID NO 164
<211> LENGTH: 22
<212> TYPE: RNA
<213> ORGANISM: Homo sapiens

<400> SEQUENCE: 164
aggcaagaug cuggcauagc ug                                               22

<210> SEQ ID NO 165
<211> LENGTH: 23
<212> TYPE: RNA
<213> ORGANISM: Homo sapiens

<400> SEQUENCE: 165
aggcagugua guuagcugau ugc                                              23

<210> SEQ ID NO 166
<211> LENGTH: 21
<212> TYPE: RNA
<213> ORGANISM: Homo sapiens

<400> SEQUENCE: 166
cuuuuugcgg ucugggcuug c                                                21

<210> SEQ ID NO 167
<211> LENGTH: 22
<212> TYPE: RNA
<213> ORGANISM: Homo sapiens

<400> SEQUENCE: 167
cagugguuuu acccuauggu ag                                               22

<210> SEQ ID NO 168
<211> LENGTH: 20
<212> TYPE: RNA
<213> ORGANISM: Mus musculus

<400> SEQUENCE: 168
uccauaaagu aggaaacacu                                                  20

<210> SEQ ID NO 169
<211> LENGTH: 22
<212> TYPE: RNA
<213> ORGANISM: Homo sapiens

<400> SEQUENCE: 169
aaaguucuga gacacuccga cu                                               22

<210> SEQ ID NO 170
<211> LENGTH: 24
<212> TYPE: RNA
<213> ORGANISM: Homo sapiens

<400> SEQUENCE: 170
uagguucugu gauacacucc gacu                                             24

<210> SEQ ID NO 171
<211> LENGTH: 22
<212> TYPE: RNA
<213> ORGANISM: Homo sapiens

<400> SEQUENCE: 171
ccuuaucacu uuuccagcca gc                                               22
```

```
<210> SEQ ID NO 172
<211> LENGTH: 23
<212> TYPE: RNA
<213> ORGANISM: Homo sapiens

<400> SEQUENCE: 172
cccaguguuc agacuaccug uuc                                              23

<210> SEQ ID NO 173
<211> LENGTH: 22
<212> TYPE: RNA
<213> ORGANISM: Homo sapiens

<400> SEQUENCE: 173
uucccuuugu cauccuaugc cu                                               22

<210> SEQ ID NO 174
<211> LENGTH: 23
<212> TYPE: RNA
<213> ORGANISM: Homo sapiens

<400> SEQUENCE: 174
accuuggcuc uagacugcuu acu                                              23

<210> SEQ ID NO 175
<211> LENGTH: 22
<212> TYPE: RNA
<213> ORGANISM: Homo sapiens

<400> SEQUENCE: 175
ugccugucua cacuugcugu gc                                               22

<210> SEQ ID NO 176
<211> LENGTH: 22
<212> TYPE: RNA
<213> ORGANISM: Homo sapiens

<400> SEQUENCE: 176
gcgacgagcc ccucgcacaa ac                                               22

<210> SEQ ID NO 177
<211> LENGTH: 22
<212> TYPE: RNA
<213> ORGANISM: Homo sapiens

<400> SEQUENCE: 177
uaugugccuu uggacuacau cg                                               22

<210> SEQ ID NO 178
<211> LENGTH: 22
<212> TYPE: RNA
<213> ORGANISM: Homo sapiens

<400> SEQUENCE: 178
gggacccggg gagagauguaa ag                                              22

<210> SEQ ID NO 179
<211> LENGTH: 22
<212> TYPE: RNA
<213> ORGANISM: Homo sapiens

<400> SEQUENCE: 179
aggagagagu uagcgcauua gu                                               22
```

```
<210> SEQ ID NO 180
<211> LENGTH: 21
<212> TYPE: RNA
<213> ORGANISM: Homo sapiens

<400> SEQUENCE: 180
cugaccuaug aauugacagc c                                              21

<210> SEQ ID NO 181
<211> LENGTH: 21
<212> TYPE: RNA
<213> ORGANISM: Homo sapiens

<400> SEQUENCE: 181
ugauugucca aacgcaauuc u                                              21

<210> SEQ ID NO 182
<211> LENGTH: 22
<212> TYPE: RNA
<213> ORGANISM: Homo sapiens

<400> SEQUENCE: 182
agaucagaag gugacugugg cu                                             22

<210> SEQ ID NO 183
<211> LENGTH: 22
<212> TYPE: RNA
<213> ORGANISM: Homo sapiens

<400> SEQUENCE: 183
cucggggauc aucaugucac ga                                             22

<210> SEQ ID NO 184
<211> LENGTH: 22
<212> TYPE: RNA
<213> ORGANISM: Homo sapiens

<400> SEQUENCE: 184
uaaggcuccu uccugugcuu gc                                             22

<210> SEQ ID NO 185
<211> LENGTH: 20
<212> TYPE: RNA
<213> ORGANISM: Homo sapiens

<400> SEQUENCE: 185
ggugggaggu gggugggca                                                 20

<210> SEQ ID NO 186
<211> LENGTH: 22
<212> TYPE: RNA
<213> ORGANISM: Homo sapiens

<400> SEQUENCE: 186
ggggcugggg ccgggacaga gc                                             22

<210> SEQ ID NO 187
<211> LENGTH: 22
<212> TYPE: RNA
<213> ORGANISM: Homo sapiens

<400> SEQUENCE: 187
```

```
ccgcucguac ucccgggggu cc                                              22

<210> SEQ ID NO 188
<211> LENGTH: 17
<212> TYPE: RNA
<213> ORGANISM: Homo sapiens

<400> SEQUENCE: 188
agcuacauug ccagcuc                                                    17

<210> SEQ ID NO 189
<211> LENGTH: 22
<212> TYPE: RNA
<213> ORGANISM: Homo sapiens

<400> SEQUENCE: 189
cccugggagg agacguggau uc                                              22

<210> SEQ ID NO 190
<211> LENGTH: 23
<212> TYPE: RNA
<213> ORGANISM: Homo sapiens

<400> SEQUENCE: 190
ccaagugcuc agaugcuugu ggu                                             23

<210> SEQ ID NO 191
<211> LENGTH: 22
<212> TYPE: RNA
<213> ORGANISM: Homo sapiens

<400> SEQUENCE: 191
caucuuccag ugcaguguug ga                                              22

<210> SEQ ID NO 192
<211> LENGTH: 22
<212> TYPE: RNA
<213> ORGANISM: Homo sapiens

<400> SEQUENCE: 192
cgucuuaccc agcaguguuu gg                                              22

<210> SEQ ID NO 193
<211> LENGTH: 22
<212> TYPE: RNA
<213> ORGANISM: Homo sapiens

<400> SEQUENCE: 193
uacucaguaa ggcauuguuc uu                                              22

<210> SEQ ID NO 194
<211> LENGTH: 22
<212> TYPE: RNA
<213> ORGANISM: Homo sapiens

<400> SEQUENCE: 194
auguaugugu gcaugaacau gu                                              22

<210> SEQ ID NO 195
<211> LENGTH: 22
<212> TYPE: RNA
<213> ORGANISM: Homo sapiens

<400> SEQUENCE: 195
```
gcuuuaacau gggguuaccu gc                                                22

<210> SEQ ID NO 196
<211> LENGTH: 23
<212> TYPE: RNA
<213> ORGANISM: Homo sapiens

<400> SEQUENCE: 196
gaaguugccc auguuauuuu ucg                                               23

<210> SEQ ID NO 197
<211> LENGTH: 22
<212> TYPE: RNA
<213> ORGANISM: Homo sapiens

<400> SEQUENCE: 197
aucccugagu guauguggug aa                                                22

<210> SEQ ID NO 198
<211> LENGTH: 22
<212> TYPE: RNA
<213> ORGANISM: Homo sapiens

<400> SEQUENCE: 198
cucacagcuc ugguccuugg ag                                                22

<210> SEQ ID NO 199
<211> LENGTH: 23
<212> TYPE: RNA
<213> ORGANISM: Homo sapiens

<400> SEQUENCE: 199 ucugguccccc ugcuucgucc ucu                                              23

<210> SEQ ID NO 200
<211> LENGTH: 22
<212> TYPE: RNA
<213> ORGANISM: Mus musculus

<400> SEQUENCE: 200
cagugguuuu acccuauggu ag                                                22

<210> SEQ ID NO 201
<211> LENGTH: 22
<212> TYPE: RNA
<213> ORGANISM: Homo sapiens

<400> SEQUENCE: 201 gggggggcagg agggggcucag gg                                              22

<210> SEQ ID NO 202
<211> LENGTH: 21
<212> TYPE: RNA
<213> ORGANISM: Homo sapiens

<400> SEQUENCE: 202
ugguuauccc uguccucuuc g                                                 21

<210> SEQ ID NO 203
<211> LENGTH: 22
<212> TYPE: RNA
<213> ORGANISM: Homo sapiens

<400> SEQUENCE: 203
ugagguagua gguugugugg uu                                    22

<210> SEQ ID NO 204
<211> LENGTH: 23
<212> TYPE: RNA
<213> ORGANISM: Homo sapiens

<400> SEQUENCE: 204
acucaaaacc uggcggcacu uuu                                   23

<210> SEQ ID NO 205
<211> LENGTH: 22
<212> TYPE: RNA
<213> ORGANISM: Homo sapiens

<400> SEQUENCE: 205
ucccugagac ccuaacuugu ga                                    22

<210> SEQ ID NO 206
<211> LENGTH: 23
<212> TYPE: RNA
<213> ORGANISM: Homo sapiens

<400> SEQUENCE: 206
agggacuuuu gggggcagau gug                                   23

<210> SEQ ID NO 207
<211> LENGTH: 22
<212> TYPE: RNA
<213> ORGANISM: Homo sapiens

<400> SEQUENCE: 207
caauuuagug ugugugauau uu                                    22

<210> SEQ ID NO 208
<211> LENGTH: 24
<212> TYPE: RNA
<213> ORGANISM: Homo sapiens

<400> SEQUENCE: 208
ucccugagac ccuuuaaccu guga                                  24

<210> SEQ ID NO 209
<211> LENGTH: 23
<212> TYPE: RNA
<213> ORGANISM: Homo sapiens

<400> SEQUENCE: 209
gggggccgau acacuguacg aga                                   23

<210> SEQ ID NO 210
<211> LENGTH: 23
<212> TYPE: RNA
<213> ORGANISM: Homo sapiens

<400> SEQUENCE: 210
uauggcuuuu uauuccuaug uga                                   23

<210> SEQ ID NO 211
<211> LENGTH: 23
<212> TYPE: RNA
<213> ORGANISM: Homo sapiens -continued

```
<400> SEQUENCE: 211
ucuacagugc acgucucc agu                                             23

<210> SEQ ID NO 212
<211> LENGTH: 23
<212> TYPE: RNA
<213> ORGANISM: Homo sapiens

<400> SEQUENCE: 212
ucuggcuccg ugucuucacu ccc                                            23

<210> SEQ ID NO 213
<211> LENGTH: 23
<212> TYPE: RNA
<213> ORGANISM: Homo sapiens

<400> SEQUENCE: 213
aacauucaac gcugucggug agu                                            23

<210> SEQ ID NO 214
<211> LENGTH: 20
<212> TYPE: RNA
<213> ORGANISM: Homo sapiens

<400> SEQUENCE: 214
ccucugggcc cuuccuccag                                                20

<210> SEQ ID NO 215
<211> LENGTH: 22
<212> TYPE: RNA
<213> ORGANISM: Homo sapiens

<400> SEQUENCE: 215
aagacgggag gaaagaaggg ag                                             22

<210> SEQ ID NO 216
<211> LENGTH: 22
<212> TYPE: RNA
<213> ORGANISM: Homo sapiens

<400> SEQUENCE: 216
aguggggaac ccuuccauga gg                                             22

<210> SEQ ID NO 217
<211> LENGTH: 22
<212> TYPE: RNA
<213> ORGANISM: Homo sapiens

<400> SEQUENCE: 217
ugagguagua gguuguaugg uu                                             22

<210> SEQ ID NO 218
<211> LENGTH: 23
<212> TYPE: RNA
<213> ORGANISM: Homo sapiens

<400> SEQUENCE: 218
ucuuugguua ucuagcugua uga                                            23

<210> SEQ ID NO 219
<211> LENGTH: 22
<212> TYPE: RNA
```

-continued

```
<213> ORGANISM: Homo sapiens

<400> SEQUENCE: 219
uagcagcaca ucaugguuua ca                                            22

<210> SEQ ID NO 220
<211> LENGTH: 22
<212> TYPE: RNA
<213> ORGANISM: Homo sapiens

<400> SEQUENCE: 220
uagcagcacg uaaauauugg cg                                            22

<210> SEQ ID NO 221
<211> LENGTH: 22
<212> TYPE: RNA
<213> ORGANISM: Homo sapiens

<400> SEQUENCE: 221
uagcuuauca gacugauguu ga                                            22

<210> SEQ ID NO 222
<211> LENGTH: 22
<212> TYPE: RNA
<213> ORGANISM: Homo sapiens

<400> SEQUENCE: 222 ggggguuccug gggaugggau uu                                           22

<210> SEQ ID NO 223
<211> LENGTH: 22
<212> TYPE: RNA
<213> ORGANISM: Homo sapiens

<400> SEQUENCE: 223
ugccuacuga gcugauauca gu                                            22

<210> SEQ ID NO 224
<211> LENGTH: 21
<212> TYPE: RNA
<213> ORGANISM: Homo sapiens

<400> SEQUENCE: 224
aggcggagac uugggcaauu g                                             21

<210> SEQ ID NO 225
<211> LENGTH: 22
<212> TYPE: RNA
<213> ORGANISM: Homo sapiens

<400> SEQUENCE: 225
agggcuuagc ugcuugugag ca                                            22

<210> SEQ ID NO 226
<211> LENGTH: 23
<212> TYPE: RNA
<213> ORGANISM: Homo sapiens

<400> SEQUENCE: 226
agguugggau cgguugcaau gcu                                           23

<210> SEQ ID NO 227
<211> LENGTH: 23
```

```
<212> TYPE: RNA
<213> ORGANISM: Homo sapiens

<400> SEQUENCE: 227
caaagugcug uucgugcagg uag                                              23

<210> SEQ ID NO 228
<211> LENGTH: 23
<212> TYPE: RNA
<213> ORGANISM: Homo sapiens

<400> SEQUENCE: 228
agcagcauug uacagggcua uga                                              23

<210> SEQ ID NO 229
<211> LENGTH: 21
<212> TYPE: RNA
<213> ORGANISM: Homo sapiens

<400> SEQUENCE: 229
uaaagugcug acagugcaga u                                                21

<210> SEQ ID NO 230
<211> LENGTH: 22
<212> TYPE: RNA
<213> ORGANISM: Homo sapiens

<400> SEQUENCE: 230
ucccugagac ccuaacuugu ga                                               22

<210> SEQ ID NO 231
<211> LENGTH: 22
<212> TYPE: RNA
<213> ORGANISM: Homo sapiens

<400> SEQUENCE: 231
ucucccaacc cuuguaccag ug                                               22

<210> SEQ ID NO 232
<211> LENGTH: 22
<212> TYPE: RNA
<213> ORGANISM: Homo sapiens

<400> SEQUENCE: 232
agccccugcc caccgcacac ug                                               22

<210> SEQ ID NO 233
<211> LENGTH: 21
<212> TYPE: RNA
<213> ORGANISM: Homo sapiens

<400> SEQUENCE: 233
cuuccgcccc gccgggcguc g                                                21

<210> SEQ ID NO 234
<211> LENGTH: 23
<212> TYPE: RNA
<213> ORGANISM: Homo sapiens

<400> SEQUENCE: 234
ucaagagcaa uaacgaaaaa ugu                                              23

<210> SEQ ID NO 235
```

```
<211> LENGTH: 21
<212> TYPE: RNA
<213> ORGANISM: Homo sapiens

<400> SEQUENCE: 235
auguaugugu gcaugugcau g                                              21

<210> SEQ ID NO 236
<211> LENGTH: 23
<212> TYPE: RNA
<213> ORGANISM: Homo sapiens

<400> SEQUENCE: 236
auacacauac acgcaacaca cau                                            23

<210> SEQ ID NO 237
<211> LENGTH: 21
<212> TYPE: RNA
<213> ORGANISM: Homo sapiens

<400> SEQUENCE: 237
cuagacugaa gcuccuugag g                                              21

<210> SEQ ID NO 238
<211> LENGTH: 21
<212> TYPE: RNA
<213> ORGANISM: Homo sapiens

<400> SEQUENCE: 238
cauuauuacu uuggguacgc g                                              21

<210> SEQ ID NO 239
<211> LENGTH: 22
<212> TYPE: RNA
<213> ORGANISM: Homo sapiens

<400> SEQUENCE: 239
aaaagcuggg uugagagggc ga                                             22

<210> SEQ ID NO 240
<211> LENGTH: 23
<212> TYPE: RNA
<213> ORGANISM: Homo sapiens

<400> SEQUENCE: 240
gagguuuucu ggguuucugu uuc                                            23

<210> SEQ ID NO 241
<211> LENGTH: 21
<212> TYPE: RNA
<213> ORGANISM: Homo sapiens

<400> SEQUENCE: 241
cagcagcaca cugugguuug u                                              21

<210> SEQ ID NO 242
<211> LENGTH: 24
<212> TYPE: RNA
<213> ORGANISM: Homo sapiens

<400> SEQUENCE: 242
acuggcuagg gaaaaugauu ggau                                           24
```

```
<210> SEQ ID NO 243
<211> LENGTH: 22
<212> TYPE: RNA
<213> ORGANISM: Homo sapiens

<400> SEQUENCE: 243
uagcuuauca gacugauguu ga                                              22

<210> SEQ ID NO 244
<211> LENGTH: 21
<212> TYPE: RNA
<213> ORGANISM: Homo sapiens

<400> SEQUENCE: 244
cauaaaguag aaagcacuac u                                               21

<210> SEQ ID NO 245
<211> LENGTH: 21
<212> TYPE: RNA
<213> ORGANISM: Homo sapiens

<400> SEQUENCE: 245
cuuuuugcgg ucugggcuug c                                               21

<210> SEQ ID NO 246
<211> LENGTH: 22
<212> TYPE: RNA
<213> ORGANISM: Homo sapiens

<400> SEQUENCE: 246
cagcagcaca cugugguuug ua                                              22
```

MICROGLIA MICROVESICLES CONTAINED MICRORNA-BASED METHODS FOR THE DIAGNOSIS, PROGNOSIS AND TREATMENT MONITORING OF NEUROLOGICAL, NEURODEGENERATIVE AND INFLAMMATION-BASED DISEASES

This is a national stage application filed under 35 U.S.C. § 371 of international application PCT/EP2016/078190, filed under the authority of the Patent Cooperation Treaty on Nov. 18, 2016, published; which claims the benefit of Italy Patent Application No. 102015000074820, filed on Nov. 20, 2015. The entire disclosures of all the aforementioned applications are expressly incorporated herein by reference for all purposes.

The present invention describes a method for the in vitro diagnosis, prognosis and/or treatment monitoring of neurodegenerative, neurological and inflammation-based diseases, wherein the method comprises the steps:
  a) isolating microglial microvesicles (MVs) from biological fluids obtained from an individual;
  b) collecting the microRNA (miRNA) contained into said MVs;
  c) determining the expression profile of a predetermined set of miRNA;
  d) comparing said expression profile to one or several reference expression profiles,
wherein the comparison of said determined expression profile to said one or several reference expression profiles allows for the diagnosis, prognosis and/or treatment monitoring of the disease.

BACKGROUND

Emerging evidence indicates that inflammation represents a pathogenic factor in many CNS diseases, including chronic neurodegenerative diseases such as Alzheimer's Disease (AD), Parkinson's Disease (PD), Amyotrophic Lateral Sclerosis (ALS), Multiple Sclerosis (MS), neurological disorders such as schizophrenia or epilepsy but also rare diseases such as Batten's Disease. Evidence indicating a role for inflammation in the early phases of brain tumors development have been reported, too (Sowers J L et al. The role of inflammation in brain cancer. Adv Exp Med Biol. 2014; 816:75-105).

Microglia, the resident immune cells in the brain, plays a crucial role in the onset of neuroinflammation. Microglial cells are the major cellular elements with immune function inside the CNS and are fundamental in orchestrating inflammatory brain responses to external challenges.

In spite of the evidence indicating that chronic inflammation might influence the pathogenesis of degenerative diseases, the mechanisms of communication between microglia and neurons have not been clearly elucidated, and it is still unclear which molecules are being released by these cells and how the damage occurs at neuronal level. Activated microglia may affect either positively or negatively neuronal survival, via the production of growth factors or pro-inflammatory mediators.

Upon cellular activation, microglia release plasma membrane-derived microvesicles (MVs) at a very early stage of the inflammatory process leading to neurodegeneration (Bianco F et al. Astrocyte-derived ATP induces vesicle shedding and IL-1 beta release from microglia. J Immunol. 2005 174(11):7268-77; Bianco F et al. Acid sphingomyelinase activity triggers microparticle release from glial cells. EMBO J. 2009 28(8):1043-54).

MVs have been found in high number in the cerebrospinal fluid of patients with mild cognitive impairment (Agosta F et al. Myeloid microvesicles in cerebrospinal fluid are associated with myelin damage and neuronal loss in mild cognitive impairment and Alzheimer disease. Ann Neurol. 2014 76(6):813-25; U.S. Pat. No. 8,999,655 B2).

MicroRNAs (miRNAs, miR) are small non-coding RNAs expressed in animals and plants. They regulate cellular function, cell survival, cell activation and cell differentiation during development. Many miRNAs are conserved in sequence between distantly related organisms.

A diagnostic method for neurodegenerative, neurological and inflammation-based diseases is strongly needed, as well as a method for monitoring the therapeutic outcome in diseases where the therapeutic protocol has to be strictly defined and punctually modified accordingly to the specific reaction observed in each treated individual.

DESCRIPTION OF THE INVENTION

The authors of the present invention have surprisingly demonstrated a strong and specific correlation between miRNA content and profile of MVs derived from microglia cells and neurodegenerative, neurological and inflammation-based diseases. The authors have surprisingly demonstrated that specific patterns of miRNAs are activated in microglial MVs derived under different detrimental conditions.

It is here firstly described a pathology and/or disease-specific miRNA profile within the microglial MVs isolated from biological fluids both for early diagnosis, prognosis and/or treatment monitoring.

A "miRNA" is a naturally occurring, small non-coding RNA that is about 17 to about 25 nucleotide (nt) in length in its biologically active form that negatively regulates mRNA translation on a sequence-specific manner. Identified miRNAs are registered in the miRNA database miRBase (http://microma.sanger.ac.uk/).

A "sample", as defined herein, is a small part of a subject, representative of the whole and may be constituted by a body fluid sample. Body fluid samples may be blood, plasma, serum, urine, sputum, cerebrospinal fluid, milk, or ductal fluid samples and may likewise be fresh, frozen or fixed. Samples may be removed surgically, by extraction i.e. by hypodermic or other types of needles, by microdissection or laser capture. The sample should contain any biological material suitable for detecting the desired biomarker (miRNA), thus, said sample should advantageously comprise cell material from the subject.

A "reference sample", as used herein, means a sample obtained from individuals, preferably two or more individuals, known to be free of any neurodegenerative, neurological disease or neuroinflammation or from the general population. The suitable reference expression levels of miRNAs can be determined by measuring the expression levels of said miRNAs in several suitable individuals, and such reference levels can be adjusted to specific populations. In a preferred embodiment, the reference sample is obtained from a pool of healthy individuals. The expression profile of the miRNAs in the reference sample can, preferably, be generated from a population of two or more individuals; for example, the population can comprise 3, 4, 5, 10, 15, 20, 30, 40, 50 or more subjects.

An "individual", as used herein, refers to a mammal, human or non-human, under observation, preferably a human being. The individual may be any individual, an individual predisposed to a neuro-related disease or an individual suffering from a neuro-related disease.

As used herein, the expression "diagnosis" or "diagnosing" relates to methods by which the skilled person can estimate and even determine whether or not an individual is suffering from a given disease or condition.

Along with diagnosis, clinical disease prognosis is also an area of great concern and interest. It is important to know the stage and rapidity of advancement of the disease in order to plan the most effective therapy. If a more accurate prognosis can be made, appropriate therapy, and in some instances less severe therapy for the patient can be chosen.

Further, the expression "method of diagnosing" as used herein relates to a method that may essentially consist of the steps mentioned below, or may include additional steps. However, it must be understood that the method, in a preferred embodiment, is a method that is carried out in vitro, i.e., it is not carried out in the human or animal body.

It has here surprisingly found that the miRNAs contained in microglial MVs, microglial MVs that can be isolated according to procedures known in the state of the art, reflect in a reproducible manner any variation from the physiological state in the CNS. CNS impairments due to neurodegenerative diseases, but also linked to neurological disorders or neuroinflammation are each linked to a very specific and reproducible miRNA profile. The variation from the physiological miRNAs profile of microglial MVs miRNAs is very sensitive to disease progression, therefore making said miRNA a very useful tool not only for an early diagnosis but also for therapeutic monitoring.

The here proposed methodology offers the great advantage to make possible a miRNA based analysis where miRNA are obtained from a single cellular subpopulation, i.e. from microglial MVs. This is extremely advantageous because the process to isolate microglial MVs allows to isolate only microglial MVs, while other methodologies currently available lead to the obtainment of vesicles from several heterogeneous cellular populations. Therefore, when data are obtained from microglial MVs their reproducibility, sensitivity and specificity is increased.

In a first embodiment, the present invention describes a method for the in vitro diagnosis or clinical disease prognosis of a neurodegenerative, neurological or inflammation-based disease, wherein the method comprises the steps:
  a) isolating microglial MVs from biological fluids obtained from an individual;
  b) collecting the miRNA contained into said MVs;
  c) determining the expression profile of a predetermined set of miRNA;
  d) comparing said expression profile to one or several reference sample expression profiles,
wherein the comparison of said determined expression profiles to said one or several reference sample expression profiles allows for the diagnosis or prognosis of the disease. In a preferred embodiment, the disease is selected form the group comprising: AD, PD, ALS, MS, Batten's Disease, Schizophrenia, Epilepsy, Neuropathic pain, Neuroinflammation, Tourette Syndrome, HD, Autism, Rett Syndrome, Depression, Ischemia, Glioblastoma, Meningitis, Traumatic Brain Injury.
Glioblastoma are included because there are evidences suggesting that subpopulations of cells within human gliomas, specifically GBM (glioblastoma multiforme), are neoplastic macrophages/microglia (Leanne C Huysentruyt et al. Hypothesis: are neoplastic macrophages/microglia present in glioblastoma multiforme? ASN Neuro. 2011; 3(4)).

In a preferred embodiment, said expression profile is determined of miRNAs selected from the group consisting of miR-125a-5p (SEQ ID 1), miR-300-3p (SEQ ID 2), miR-330-3p (SEQ ID 3), miR-466n-3p (SEQ ID 4), miR-501-5p (SEQ ID 5), miR-146a-5p (SEQ ID 6), miR-24-1-5p (SEQ ID 7), miR-1306-5p (SEQ ID 8), miR-744-5p (SEQ ID 9), miR-671-5p (SEQ ID 10), miR-134-5p (SEQ ID 11), miR-877-5p (SEQ ID 12), miR-23b-5p (SEQ ID 13), miR-669c-5p (SEQ ID 14), miR-29b-3p (SEQ ID 15), miR-195a-5p (SEQ ID 16), miR-151-5p (SEQ ID 17), miR-374c-3p (SEQ ID 18), miR-6539 (SEQ ID 19), miR-16-1-3p (SEQ ID 20), miR-6399 (SEQ ID 21), miR-6240 (SEQ ID 22), miR-23a-5p (SEQ ID 23), miR-92a-1-5p (SEQ ID 24), miR-219a-1-3p (SEQ ID 25), miR-128-1-5p (SEQ ID 26), miR-1949 (SEQ ID 27), miR-872-3p (SEQ ID 28), miR-582-3p (SEQ ID 29), miR-338-5p (SEQ ID 30), miR-379-5p (SEQ ID 31), miR-155-5p (SEQ ID 32), miR-450a-5p (SEQ ID 33), miR-100-5p (SEQ ID 34), miR-152-3p (SEQ ID 35), miR-222-3p (SEQ ID 36), let-7e (SEQ ID 37), miR-18b (SEQ ID 38), miR-19a (SEQ ID 39), miR-21b (SEQ ID 40), miR-26b (SEQ ID 41), miR-29b-1 (SEQ ID 42), miR-30c-1 (SEQ ID 43), miR-100 (SEQ ID 44), miR-130a (SEQ ID 45), miR-181c (SEQ ID 46), miR-297a-1 (SEQ ID 47), miR-330 (SEQ ID 48), miR-342 (SEQ ID 49), miR-484 (SEQ ID 50), miR-669b (SEQ ID 51), miR-669e (SEQ ID 52), miR-708 (SEQ ID 53), miR-146b (SEQ ID 54), miR-188 (SEQ ID 55), miR-346 (SEQ ID 56), miR-466f-3 (SEQ ID 57), miR-541 (SEQ ID 58), miR-706 (SEQ ID 59), miR-712 (SEQ ID 60), miR-714 (SEQ ID 61), miR-1224 (SEQ ID 62), miR-10b (SEQ ID 63), mir-22 (SEQ ID 64), mir-23b (SEQ ID 65), mir-132 (SEQ ID 66), mir-148b (SEQ ID 67), mir-154 (SEQ ID 68), mir-183 (SEQ ID 69), mir-337 (SEQ ID 70), mir-19b-1 (SEQ ID 71), mir-30a (SEQ ID 72), mir-33 (SEQ ID 73), mir-99b (SEQ ID 74), mir-144 (SEQ ID 75), mir-151 (SEQ ID 76), mir-182 (SEQ ID 77), mir-223 (SEQ ID 78), mir-340 (SEQ ID 79), mir-374b (SEQ ID 80), mir-432 (SEQ ID 81), mir-1247 (SEQ ID 82), let-7a-2 (SEQ ID 83), mir-30b (SEQ ID 84), mir-103-2 (SEQ ID 85), mir-107 (SEQ ID 86), mir-142a (SEQ ID 87), mir-146a (SEQ ID 88), mir-374c (SEQ ID 89), mir-126b (SEQ ID 90), mir-134 (SEQ ID 91), mir-320 (SEQ ID 92), let-7a-1 (SEQ ID 93), mir-34a (SEQ ID 94), mir-92b (SEQ ID 95), mir-211 (SEQ ID 96), let-7f-1 (SEQ ID 97), mir-19b-2 (SEQ ID 98), mir-137 (SEQ ID 99), mir-155 (SEQ ID 100), mir-219b (SEQ ID 101), mir-338 (SEQ ID 102), mir-376c (SEQ ID 103), mir-379 (SEQ ID 104), mir-451a (SEQ ID 105), mir-494 (SEQ ID 106), mir-17 (SEQ ID 107), mir-20a (SEQ ID 108), let-7c-1 (SEQ ID 109), mir-20b (SEQ ID 110), mir-145a (SEQ ID 111), mir-186 (SEQ ID 112), mir-664 (SEQ ID 113), mir-122 (SEQ ID 114), mir-409 (SEQ ID 115), miR-199b (SEQ ID 116), mir-221 (SEQ ID 117), mir-296 (SEQ ID 118), mir-329 (SEQ ID 119), mir-382 (SEQ ID 120), mir-29c (SEQ ID 121), mir-128-1 (SEQ ID 122), mir-138-1 (SEQ ID 123), mir-218-1 (SEQ ID 124), mir-222 (SEQ ID 125), mir-344-1 (SEQ ID 126), mir-466b-2 (SEQ ID 127), mir-674 (SEQ ID 128), mir-207 (SEQ ID 129), mir-18a (SEQ ID 130), mir-448 (SEQ ID 131), mir-146b-3 (SEQ ID 132), mir-669c (SEQ ID 133), let-7d (SEQ ID 134), mir-30e (SEQ ID 135), mir-34b (SEQ ID 136), mir-(SEQ ID 137), mir-124-1 (SEQ ID 138), mir-181a-1 (SEQ ID 139), mir-181b-1 (SEQ ID 140), mir-181d (SEQ ID 141), mir-185 (SEQ ID 142), mir-187 (SEQ ID 143), mir-190a (SEQ ID 144), mir-191 (SEQ ID 145), mir-301a (SEQ ID 146), mir-325 (SEQ ID 147), mir-331 (SEQ ID 148), mir-345 (SEQ ID 149), mir-361 (SEQ ID 150), mir-380 (SEQ ID 151), mir-381 (SEQ ID 152), mir-450a-2 (SEQ ID 153), mir-497a (SEQ ID 246), mir-497b (SEQ ID 155), mir-505 (SEQ ID 156), mir-551b (SEQ ID 157), mir-742 (SEQ ID 158), mir-875 (SEQ ID 159), mir-935 (SEQ ID 160), mir-21a (SEQ ID 161), mir-24-2 (SEQ ID 162), mir-27b (SEQ ID 163), mir-31 (SEQ ID 164), mir-34c (SEQ ID 165), mir-129-1 (SEQ ID 166), mir-140 (SEQ ID 167), mir-142b (SEQ ID 168), mir-148a (SEQ ID 169), mir-152 (SEQ ID 170), mir-184 (SEQ ID 171), mir-199a-1 (SEQ ID 172), mir-204 (SEQ ID 173), mir-212 (SEQ ID 174), mir-214 (SEQ ID 175), mir-375 (SEQ ID 176), mir-455 (SEQ ID 177), mir-711 (SEQ ID 178), mir-882 (SEQ ID 179), mir-192 (SEQ ID 180), mir-219a-1 (SEQ ID 181), mir-383 (SEQ ID 182), mir-542 (SEQ ID 183), mir-700 (SEQ ID 184), mir-705 (SEQ ID 185), mir-762 (SEQ ID 186), mir-1901 (SEQ ID 187), mir-1928 (SEQ ID 188), mir-3474 (SEQ ID 189), mir-105 (SEQ ID 190), mir-141 (SEQ ID 191), mir-200c (SEQ ID 192), mir-201 (SEQ ID 193), mir-297b (SEQ ID 194), mir-302c (SEQ ID 195), mir-495 (SEQ ID 196), mir-670 (SEQ ID 197), mir-673 (SEQ ID 198), mir-1934 (SEQ ID 199), mir-129b (SEQ ID 200), mir-328 (SEQ ID 201), mir-487b (SEQ ID 202), let-7b (SEQ ID 203), mir-292b (SEQ ID 204), mir-125b-2 (SEQ ID 205), mir-365-1 (SEQ ID 206), mir-32 (SEQ ID 207), mir-125a (SEQ ID 208), mir-128-2 (SEQ ID 209), mir-135a-1 (SEQ ID 210), mir-139 (SEQ ID 211), mir-149 (SEQ ID 212), mir-181a-2 (SEQ ID 213), mir-326 (SEQ ID 214), mir-483 (SEQ ID 215), mir-491 (SEQ ID 216), let-7c (SEQ ID 217), mir-9-1 (SEQ ID 218), mir-15b (SEQ ID 219), mir-16-1 (SEQ ID 220), mir-21 (SEQ ID 221), mir-23a (SEQ ID 222), mir-24-1 (SEQ ID 223), mir-25 (SEQ ID 224), mir-27a (SEQ ID 225), mir-92a-1 (SEQ ID 226), mir-93 (SEQ ID 227), mir-103a-1 (SEQ ID 228), mir-106b (SEQ ID 229), mir-125b-1 (SEQ ID 230), mir-150 (SEQ ID 231), mir-210 (SEQ ID 232), mir-718 (SEQ ID 233), mir-335 (SEQ ID 234), mir-297 (SEQ ID 235), mir-466 (SEQ ID 236), mir-151a (SEQ ID 237), mir-126 (SEQ ID 238), mir-320a (SEQ ID 239), mir-329-5p (SEQ ID 240), mir-497-5p (SEQ ID 241), mir-664a-5p (SEQ ID 242), mir-21-5p (SEQ ID 243), mir-142-5p (SEQ ID 244), mir-129-5p (SEQ ID 245), mir-146b (SEQ ID 154).

In a further preferred embodiment, said method is a method for diagnosis or prognosis of PD in an individual, wherein a pattern of at least 11 up-regulated and least 7 down-regulated specific miRNAs listed above is an indicator of PD, preferably said pattern is the pattern listed in Table 1.

TABLE 1

| PD, microglial MVs miRNA pattern (+, upregulated; −, downregulated) | |
|---|---|
| miRNA | |
| miR-100-5p (SEQ ID 34) | − |
| miR-128-1-5p (SEQ ID 26) | + |
| miR-152-3p (SEQ ID 35) | − |
| miR-155-5p (SEQ ID 32) | − |
| miR-16-1-3p (SEQ ID 20) | + |
| miR-1949 (SEQ ID 27) | − |
| miR-219a-1-3p (SEQ ID 25) | + |
| miR-222-3p (SEQ ID 36) | + |
| miR-23a-5p (SEQ ID 23) | + |
| miR-338-5p (SEQ ID 30) | + |
| miR-379-5p (SEQ ID 31) | + |
| miR-450a-5p (SEQ ID 33) | + |
| miR-501-5p (SEQ ID 5) | − |
| miR-582-3p (SEQ ID 29) | + |
| miR-6240 (SEQ ID 22) | + |
| miR-6399 (SEQ ID 21) | − |
| miR-872-3p (SEQ ID 28) | − |
| miR-92a-1-5p (SEQ ID 24) | + |

In a preferred embodiment, said pattern is the pattern listed in Table 1a.

TABLE 1a

| PD, microglial MVs miRNA pattern (+, upregulated; −, downregulated) | |
|---|---|
| miRNA | |
| miR-100-5p (SEQ ID 34) | − |
| miR-128-1-5p (SEQ ID 26) | + |
| miR-152-3p (SEQ ID 35) | − |
| miR-155-5p (SEQ ID 32) | − |
| miR-16-1-3p (SEQ ID 20) | + |
| miR-219a-1-3p (SEQ ID 25) | + |
| miR-222-3p (SEQ ID 36) | + |
| miR-23a-5p (SEQ ID 23) | + |
| miR-338-5p (SEQ ID 30) | + |
| miR-379-5p (SEQ ID 31) | + |
| miR-450a-5p (SEQ ID 33) | + |
| miR-501-5p (SEQ ID 5) | − |
| miR-582-3p (SEQ ID 29) | + |
| miR-92a-1-5p (SEQ ID 24) | + |

In a further preferred embodiment, said method is a method for diagnosis or prognosis of AD in an individual, wherein a pattern of at least 12 up-regulated and at least 4 down-regulated specific miRNAs listed above is an indicator of AD, preferably said pattern is the pattern listed in Table 2.

TABLE 2

| AD, microglial MVs pattern (+, upregulated; −, downregulated) | |
|---|---|
| miRNA | |
| miR-501-5p (SEQ ID 5) | + |
| miR-125a-5p (SEQ ID 1) | + |
| miR-1306-5p (SEQ ID 8) | + |
| miR-134-5p (SEQ ID 11) | + |
| miR-146a-5p (SEQ ID 6) | + |
| miR-151-5p (SEQ ID 17) | − |
| miR-23b-5p (SEQ ID 13) | − |
| miR-24-1-5p (SEQ ID 7) | + |
| miR-300-3p (SEQ ID 2) | + |
| miR-330-3p (SEQ ID 3) | + |
| miR-374c-3p (SEQ ID 18) | − |
| miR-466n-3p (SEQ ID 4) | + |
| miR-669c-5p (SEQ ID 14) | − |
| miR-671-5p (SEQ ID 10) | + |
| miR-744-5p (SEQ ID 9) | + |
| miR-877-5p (SEQ ID 12) | + |

In a preferred embodiment, said pattern is the pattern listed in Table 2a.

TABLE 2a

| AD, microglial MVs pattern (+, upregulated; −, downregulated) | |
|---|---|
| miRNA | |
| miR-501-5p (SEQ ID 5) | + |
| miR-125a-5p (SEQ ID 1) | + |
| miR-1306-5p (SEQ ID 8) | + |
| miR-134-5p (SEQ ID 11) | + |
| miR-146a-5p (SEQ ID 6) | + |
| miR-151-5p (SEQ ID 17) | − |
| miR-23b-5p (SEQ ID 13) | − |
| miR-24-1-5p (SEQ ID 7) | + |
| miR-300-3p (SEQ ID 2) | + |
| miR-330-3p (SEQ ID 3) | + |
| miR-374c-3p (SEQ ID 18) | − |
| miR-671-5p (SEQ ID 10) | + |

TABLE 2a-continued

AD, microglial MVs pattern
(+, upregulated; −, downregulated)

| miRNA | |
|---|---|
| miR-744-5p (SEQ ID 9) | + |
| miR-877-5p (SEQ ID 12) | + |

In a further preferred embodiment, said method is a method for diagnosis or prognosis of ischemia in an individual, wherein a pattern of at least 16, more preferably at least 20 of the miRNA listed in Table 3 is an indicator of ischemia, still more preferably said pattern is the pattern listed in Table 3.

TABLE 3 ischemia, microglial MVs pattern
(+, upregulated; −, downregulated)

| miRNA | |
|---|---|
| let-7e (SEQ ID 37) | − |
| mir-18b (SEQ ID 38) | − |
| mir-19a (SEQ ID 39) | − |
| mir-21 (SEQ ID 221) | − |
| mir-26b (SEQ ID 41) | − |
| mir-29b-1 (SEQ ID 42) | − |
| mir-30c-1 (SEQ ID 43) | − |
| mir-100 (SEQ ID 44) | − |
| mir-130a (SEQ ID 45) | − |
| mir-181c (SEQ ID 46) | − |
| mir-297 (SEQ ID 235) | − |
| mir-330 (SEQ ID 48) | − |
| mir-342 (SEQ ID 49) | − |
| mir-484 (SEQ ID 50) | − |
| mir-669b (SEQ ID 51) | − |
| mir-669e (SEQ ID 52) | − |
| mir-708 (SEQ ID 53) | − |
| mir-146b (SEQ ID 54) | + |
| mir-188 (SEQ ID 55) | + |
| mir-346 (SEQ ID 56) | + |
| mir-466 (SEQ ID 236) | + |
| mir-541 (SEQ ID 58) | + |
| mir-706 (SEQ ID 59) | + |
| mir-712 (SEQ ID 60) | + |
| mir-714 (SEQ ID 61) | + |
| mir-1224 (SEQ ID 62) | + |

In a further preferred embodiment, said method is a method for diagnosis or prognosis of Tourette's Syndrome in an individual, wherein a pattern of at least 13, preferably at least 16 of the miRNA listed in Table 4 is an indicator of Tourette's Syndrome, preferably said pattern is the pattern listed in Table 4.

TABLE 4

Tourette's Syndrome, microglial MVs pattern
(+, upregulated; −, downregulated)

| miRNA | |
|---|---|
| mir-10b (SEQ ID 63) | − |
| mir-22 (SEQ ID 64) | − |
| mir-23b (SEQ ID 65) | − |
| mir-132 (SEQ ID 66) | − |
| mir-148b (SEQ ID 67) | − |
| mir-154 (SEQ ID 68) | − |
| mir-183 (SEQ ID 69) | − |
| mir-337 (SEQ ID 70) | − |
| mir-1224 (SEQ ID 62) | − |
| mir-19b-1 (SEQ ID 71) | + |
| mir-30a (SEQ ID 72) | + |
| mir-33 (SEQ ID 73) | + |

TABLE 4-continued

Tourette's Syndrome, microglial MVs pattern
(+, upregulated; −, downregulated)

| miRNA | |
|---|---|
| mir-99b (SEQ ID 74) | + |
| mir-144 (SEQ ID 75) | + |
| mir-151a (SEQ ID 237) | + |
| mir-182 (SEQ ID 77) | + |
| mir-223 (SEQ ID 78) | + |
| mir-340 (SEQ ID 79) | + |
| mir-374b (SEQ ID 80) | + |
| mir-432 (SEQ ID 81) | + |
| mir-1247 (SEQ ID 82) | + |

In a further preferred embodiment, said method is a method for diagnosis or prognosis of neuropathic pain in an individual, wherein a pattern of at least 8, preferably at least 10 of the miRNA listed in Table 5 is an indicator of neuropathic pain, preferably said pattern is the pattern listed in Table 5.

TABLE 5

Neurophatic pain, microglial MVs pattern
(+, upregulated; −, downregulated)

| miRNA | |
|---|---|
| let-7a-2 (SEQ ID 83) | − |
| mir-30b (SEQ ID 84) | − |
| mir-103-2 (SEQ ID 85) | − |
| mir-107 (SEQ ID 86) | − |
| mir-142a (SEQ ID 87) | − |
| mir-146a (SEQ ID 88) | − |
| mir-151 (SEQ ID 76) | − |
| mir-374c (SEQ ID 89) | − |
| mir-126 (SEQ ID 238) | + |
| mir-134 (SEQ ID 91) | + |
| mir-320a (SEQ ID 239) | + |
| mir-374b (SEQ ID 80) | + |

In a further preferred embodiment, said method is a method for diagnosis or prognosis of autism in an individual, wherein a pattern of at least 13, preferably at least 16 of the miRNA listed in Table 6 is an indicator of autism, preferably said pattern is the pattern listed in Table 6.

TABLE 6

Autism, microglial MVs pattern
(+, upregulated; −, downregulated)

| miRNA | |
|---|---|
| let-7a-1 (SEQ ID 93) | − |
| mir-34a (SEQ ID 94) | − |
| mir-92b (SEQ ID 95) | − |
| mir-211 (SEQ ID 96) | − |
| let-7f-1 (SEQ ID 97) | + |
| mir-19a (SEQ ID 39) | + |
| mir-19b-2 (SEQ ID 98) | + |
| mir-21 (SEQ ID 221) | + |
| mir-22 (SEQ ID 64) | + |
| mir-137 (SEQ ID 99) | + |
| mir-142a (SEQ ID 87) | + |
| mir-144 (SEQ ID 75) | + |
| mir-146b (SEQ ID 154) | + |
| mir-155 (SEQ ID 100) | + |
| mir-219b (SEQ ID 101) | + |
| mir-338 (SEQ ID 102) | + |
| mir-376c (SEQ ID 103) | + |
| mir-379 (SEQ ID 104) | + |
| mir-451a (SEQ ID 105) | + |
| mir-494 (SEQ ID 106) | + |

In a further preferred embodiment, said method is a method for diagnosis or prognosis of multiple sclerosis in an individual, wherein a pattern of at least 7 of the miRNA listed in Table 7 is an indicator of multiple sclerosis, preferably said pattern is the pattern listed in Table 7.

TABLE 7 multiple sclerosis, microglial MVs pattern
(+, upregulated; −, downregulated)

| miRNA | |
|---|---|
| mir-17 (SEQ ID 107) | − |
| mir-20a (SEQ ID 108) | − |
| let-7c-1 (SEQ ID 109) | + |
| mir-20b (SEQ ID 110) | + |
| mir-142a (SEQ ID 87) | + |
| mir-145a (SEQ ID 111) | + |
| mir-186 (SEQ ID 112) | + |
| mir-223 (SEQ ID 78) | + |
| mir-664 (SEQ ID 113) | + |

In a further preferred embodiment, said method is a method for diagnosis or prognosis of Rett Syndrome in an individual, wherein a pattern of at least 10 of the miRNA listed in Table 8 is an indicator of Rett Syndrome, preferably said pattern is the pattern listed in Table 8.

TABLE 8

Rett Syndrome, microglial MVs pattern
(+, upregulated; −, downregulated)

| miRNA | |
|---|---|
| mir-122 (SEQ ID 114) | − |
| mir-130a (SEQ ID 45) | − |
| mir-146a (SEQ ID 88) | − |
| mir-146b (SEQ ID 54) | − |
| mir-342 (SEQ ID 49) | − |
| mir-409 (SEQ ID 115) | − |
| mir-29b-1 (SEQ ID 42) | + |
| mir-92b (SEQ ID 95) | + |
| mir-199b (SEQ ID 116) | + |
| mir-221 (SEQ ID 117) | + |
| mir-296 (SEQ ID 118) | + |
| mir-329-5p (SEQ ID 240) | + |
| mir-382 (SEQ ID 120) | + |

In a further preferred embodiment, said method is a method for diagnosis or prognosis of Huntington's Disease in an individual, wherein a pattern of at least 12 of the miRNA listed in Table 9 is an indicator of Huntington's Disease, preferably said pattern is the pattern listed in Table 9.

TABLE 9

Huntington's Disease, microglial MVs pattern
(+, upregulated; −, downregulated)

| miRNA | |
|---|---|
| mir-22 (SEQ ID 64) | − |
| mir-29c (SEQ ID 121) | − |
| mir-128-1 (SEQ ID 122) | − |
| mir-132 (SEQ ID 66) | − |
| mir-138-1 (SEQ ID 123) | − |
| mir-218-1 (SEQ ID 124) | − |
| mir-222 (SEQ ID 125) | − |
| mir-344-1 (SEQ ID 126) | − |
| mir-466 (SEQ ID 236) | − |
| mir-674 (SEQ ID 128) | − |
| mir-34a (SEQ ID 94) | + |
| mir-207 (SEQ ID 129) | + |

TABLE 9-continued

Huntington's Disease, microglial MVs pattern
(+, upregulated; −, downregulated)

| miRNA | |
|---|---|
| mir-18a (SEQ ID 130) | + |
| mir-448 (SEQ ID 131) | + |
| mir-669c (SEQ ID 133) | + |

In a further preferred embodiment, said method is a method for diagnosis or prognosis of epilepsy in an individual, wherein a pattern of at least 31, preferably at least 42 of the miRNA listed in Table 10 is an indicator of epilepsy, preferably said pattern is the pattern listed in Table 10.

TABLE 10 epilepsy, microglial MVs pattern
(+, upregulated; −, downregulated)

| miRNA | |
|---|---|
| let-7d (SEQ ID 134) | − |
| let-7f-1 (SEQ ID 97) | − |
| mir-30a (SEQ ID 72) | − |
| mir-30e (SEQ ID 135) | − |
| mir-34b (SEQ ID 136) | − |
| mir-98 (SEQ ID 137) | − |
| mir-124-1 (SEQ ID 138) | − |
| mir-181a-1 (SEQ ID 139) | − |
| mir-181b-1 (SEQ ID 140) | − |
| mir-181d (SEQ ID 141) | − |
| mir-185 (SEQ ID 142) | − |
| mir-186 (SEQ ID 112) | − |
| mir-187 (SEQ ID 143) | − |
| mir-190a (SEQ ID 144) | − |
| mir-191 (SEQ ID 145) | − |
| mir-301a (SEQ ID 146) | − |
| mir-325 (SEQ ID 147) | − |
| mir-331 (SEQ ID 148) | − |
| mir-345 (SEQ ID 149) | − |
| mir-361 (SEQ ID 150) | − |
| mir-374b (SEQ ID 80) | − |
| mir-380 (SEQ ID 151) | − |
| mir-381 (SEQ ID 152) | − |
| mir-450a-2 (SEQ ID 153) | − |
| mir-497a (SEQ ID 246) | − |
| mir-497-5p (SEQ ID 241) | − |
| mir-505 (SEQ ID 156) | − |
| mir-551b (SEQ ID 157) | − |
| mir-664a-5p (SEQ ID 242) | − |
| mir-742 (SEQ ID 158) | − |
| mir-875 (SEQ ID 159) | − |
| mir-935 (SEQ ID 160) | − |
| mir-17 (SEQ ID 107) | + |
| mir-21-5p (SEQ ID 243) | + |
| mir-23b (SEQ ID 65) | + |
| mir-24-2 (SEQ ID 162) | + |
| mir-27b (SEQ ID 163) | + |
| mir-31 (SEQ ID 164) | + |
| mir-34c (SEQ ID 165) | + |
| mir-129-1 (SEQ ID 166) | + |
| mir-140 (SEQ ID 167) | + |
| mir-142-5p (SEQ ID 244) | + |
| mir-148a (SEQ ID 169) | + |
| mir-152 (SEQ ID 170) | + |
| mir-184 (SEQ ID 171) | + |
| mir-199a-1 (SEQ ID 172) | + |
| mir-204 (SEQ ID 173) | + |
| mir-212 (SEQ ID 174) | + |
| mir-214 (SEQ ID 175) | + |
| mir-375 (SEQ ID 176) | + |
| mir-455 (SEQ ID 177) | + |
| mir-711 (SEQ ID 178) | + |
| mir-882 (SEQ ID 179) | + |

In a further preferred embodiment, said method is a method for diagnosis of glioblastoma in an individual, wherein a pattern of at least 33, preferably of at least 44 of the miRNA listed in Table 11 is an indicator of glioblastoma, preferably said pattern is the pattern listed in Table 11.

TABLE 11 glioblastoma, MVs pattern
(+, upregulated; −, downregulated)

| miRNA | |
|---|---|
| mir-29b-1 (SEQ ID 42) | − |
| mir-32 (SEQ ID 207) | − |
| mir-34a (SEQ ID 94) | − |
| mir-100 (SEQ ID 44) | − |
| mir-124-1 (SEQ ID 138) | − |
| mir-125a (SEQ ID 208) | − |
| mir-128-1 (SEQ ID 122) | − |
| mir-128-2 (SEQ ID 209) | − |
| mir-129-1 (SEQ ID 166) | − |
| mir-132 (SEQ ID 66) | − |
| mir-135a-1 (SEQ ID 210) | − |
| mir-137 (SEQ ID 99) | − |
| mir-138-1 (SEQ ID 123) | − |
| mir-139 (SEQ ID 211) | − |
| mir-146b (SEQ ID 54) | − |
| mir-149 (SEQ ID 212) | − |
| mir-181a-2 (SEQ ID 213) | − |
| mir-181b-1 (SEQ ID 140) | − |
| mir-181d (SEQ ID 141) | − |
| mir-184 (SEQ ID 171) | − |
| mir-185 (SEQ ID 142) | − |
| mir-218-1 (SEQ ID 124) | − |
| mir-326 (SEQ ID 214) | − |
| mir-483 (SEQ ID 215) | − |
| mir-491 (SEQ ID 216) | − |
| let-7c (SEQ ID 217) | + |
| mir-9-1 (SEQ ID 218) | + |
| mir-15b (SEQ ID 219) | + |
| mir-16-1 (SEQ ID 220) | + |
| mir-17 (SEQ ID 107) | + |
| mir-19b-1 (SEQ ID 71) | + |
| mir-20a (SEQ ID 108) | + |
| mir-21 (SEQ ID 221) | + |
| mir-23a (SEQ ID 222) | + |
| mir-24-1 (SEQ ID 223) | + |
| mir-25 (SEQ ID 224) | + |
| mir-27a (SEQ ID 225) | + |
| mir-30b (SEQ ID 84) | + |
| mir-92a-1 (SEQ ID 226) | + |
| mir-93 (SEQ ID 227) | + |
| mir-103a-1 (SEQ ID 228) | + |
| mir-106b (SEQ ID 229) | + |
| mir-125b-1 (SEQ ID 230) | + |
| mir-146a (SEQ ID 88) | + |
| mir-150 (SEQ ID 231) | + |
| mir-155 (SEQ ID 100) | + |
| mir-182 (SEQ ID 77) | + |
| mir-183 (SEQ ID 69) | + |
| mir-210 (SEQ ID 232) | + |
| mir-221 (SEQ ID 117) | + |
| mir-223 (SEQ ID 78) | + |
| mir-328 (SEQ ID 201) | + |
| mir-381 (SEQ ID 152) | + |
| mir-451a (SEQ ID 105) | + |
| mir-718 (SEQ ID 233) | + |
| mir-335 (SEQ ID 234) | + |

In a further preferred embodiment, said method is a method for diagnosis or prognosis of meningitis in an individual, wherein a pattern of at least 16, preferably of at least 21 of the miRNA listed in Table 12 is an indicator of meningitis, preferably said pattern is the pattern listed in Table 12.

TABLE 12 meningitis, microglial MVs pattern
(+, upregulated; −, downregulated)

| miRNA | |
|---|---|
| mir-138-1 (SEQ ID 123) | − |
| mir-192 (SEQ ID 180) | − |
| mir-219a-1 (SEQ ID 181) | − |
| mir-383 (SEQ ID 182) | − |
| mir-466 (SEQ ID 236) | − |
| mir-542 (SEQ ID 183) | − |
| mir-700 (SEQ ID 184) | − |
| mir-705 (SEQ ID 185) | − |
| mir-762 (SEQ ID 186) | − |
| mir-1901 (SEQ ID 187) | − |
| mir-1928 (SEQ ID 188) | − |
| mir-3474 (SEQ ID 189) | − |
| let-7a-1 (SEQ ID 93) | + |
| mir-10b (SEQ ID 63) | + |
| mir-105 (SEQ ID 190) | + |
| mir-141 (SEQ ID 191) | + |
| mir-155 (SEQ ID 100) | + |
| mir-191 (SEQ ID 145) | + |
| mir-200c (SEQ ID 192) | + |
| mir-201 (SEQ ID 193) | + |
| mir-214 (SEQ ID 175) | + |
| mir-297b (SEQ ID 194) | + |
| mir-302c (SEQ ID 195) | + |
| mir-495 (SEQ ID 196) | + |
| mir-670 (SEQ ID 197) | + |
| mir-673 (SEQ ID 198) | + |
| mir-1934 (SEQ ID 199) | + |

In a further preferred embodiment, said method is a method for diagnosis or prognosis of traumatic brain injury in an individual, wherein a pattern of at least 12 of the miRNA listed in Table 13 is an indicator of traumatic brain injury, preferably said pattern is the pattern listed in Table 13.

TABLE 13 traumatic brain injury, microglial MVs pattern
(+, upregulated; −, downregulated)

| miRNA | |
|---|---|
| mir-129-5p (SEQ ID 245) | − |
| mir-140 (SEQ ID 167) | − |
| mir-185 (SEQ ID 142) | − |
| mir-212 (SEQ ID 174) | − |
| mir-328 (SEQ ID 201) | − |
| mir-361 (SEQ ID 150) | − |
| mir-487b (SEQ ID 202) | − |
| let-7a-2 (SEQ ID 83) | + |
| let-7b (SEQ ID 203) | + |
| mir-19b-1 (SEQ ID 71) | + |
| mir-21-5p (SEQ ID 243) | + |
| mir-126 (SEQ ID 238) | + |
| mir-146a (SEQ ID 88) | + |
| mir-155 (SEQ ID 100) | + |
| mir-223 (SEQ ID 78) | + |
| mir-292b (SEQ ID 204) | + |

In a further preferred embodiment, said method is a method for diagnosis or prognosis of ALS in an individual, wherein a pattern of at least 4 of the miRNA listed in Table 14 is an indicator of ALS, preferably said pattern is the pattern listed in Table 14.

TABLE 14

ALS, microglial MVs pattern (+, upregulated)

| miRNA | |
|---|---|
| mir-22 (SEQ ID 64) | + |
| mir-125b-2 (SEQ ID 205) | + |
| mir-146b (SEQ ID 54) | + |
| mir-155 (SEQ ID 100) | + |
| mir-214 (SEQ ID 175) | + |
| mir-365-1 (SEQ ID 206) | + |

In a further preferred embodiment, said method is a method for diagnosis or prognosis of depression in an individual, wherein a pattern of at least 5 of the miRNA listed in Table 15 is an indicator of depression, preferably said pattern is the pattern listed in Table 15.

TABLE 15 depression, microglial MVs pattern (+, upregulated)

| miRNA | |
|---|---|
| mir-34a (SEQ ID 94) | − |
| mir-451a (SEQ ID 105) | − |
| mir-132 (SEQ ID 66) | + |
| mir-134 (SEQ ID 91) | + |
| mir-144 (SEQ ID 75) | + |
| mir-182 (SEQ ID 77) | + |
| mir-221 (SEQ ID 117) | + |

The expression levels of a plurality of miRNAs are determined as expression level values and, in a further preferred embodiment, said step d) comprises mathematically combining the expression level values of said plurality miRNAs by applying an algorithm to obtain a normalized expression level relative to at least one reference pattern of expression levels.

In a preferred embodiment, the determination of the expression profile in said step c) is obtained by the use of a method selected from the group consisting of a Sequencing-based method, an array based method and a PCR based method.

In a further aspect, a kit for diagnosis and prognosis of neurodegenerative, neurological and inflammation-based diseases is described, comprising:
a) means for determining the miRNA expression profile of a miRNA sample of microglial microvesicles of a subject, and
b) at least one reference set of miRNA profile characteristic for a particular condition.

EXAMPLES

Materials and Methods

Microglial Cell Cultures

Microglial cells were obtained from mixed glial cultures of P2 postnatal CD1 mice (Harlan Laboratories). Cortices were isolated in ice-cold balanced salt solution (HBSS) without $Ca^{++}$ and $Mg^{++}$. Brains were collected and meninges were manually removed under dissecting microscopes under sterile hood. The tissues were then finely chopped using a scalpel. All of these operations were carried out at 4° C.

The tissue fragments were incubated at 37° C. for 20-30 min in a HBSS solution with 2.5 mg/ml trypsin, 0.2 mg/ml EDTA, 1 mg/ml glucose and 0.1 mg/ml bovine pancreatic DNase I in persistent gentle shaking in a water bath incubator.

Following incubation, fresh culture medium (DMEM/F12 (3:1) containing 20% heat-inactivated fetal bovine serum, 100 U/ml penicillin-streptomycin was added, and the suspension was centrifuged at 1500 rpm for 5 min at 4° C. Finally, single cell suspension was obtained by manual resuspension of the pellet using a sterile Pasteur pipette.

The dissociated cells were plated onto poly-L-lysine coated flasks supplemented with 20% heat-inactivated fetal bovine serum and 100 U/ml penicillin, 10 mg/ml streptomycin, and 5.5 g/L glucose (glial medium). Purified microglial cultures were harvested by shaking 3-week-old mixed glial cultures. Detached microglia was seeded on poly-L-lysine-coated flasks.

Purity of microglial cultures was carried out by immunocytochemical analysis of specific cellular markers: Antibodies against glial fibrillary acidic protein (GFAP) (1:400) for astrocytes, IB4 (1:100) for microglia, olig2 for oligodendrocytes.

Abeta Amyloid Preparation

Beta Amyloid 1-42 (American Peptide) is prepared as recommended in the data sheet and in literature; briefly the lyophilized peptide is dissolved in HPLC grade water at 6 mg/mL and then diluted to 1 mg/mL with PBS 1× without Calcium and Magnesium. After 48 h of incubation (37° C.) the peptide is incubated with the cells at a final concentration of 5 µM.

Isolation of CSF MVs

Approximately 4,500,000 cells/condition were primed with the different experimental stimuli (5 µM of Abeta oligomers for 24 hours to model AD, 1 hour of 20 µM 6-OHDA to model PD, exposure for 2 hours to oxygen glucose deprivation protocol to model ischemia, exposure to GABA-A antagonist such as 100 µM bicuculline for 2 hours to model Tourette's Syndrome, challenge the primary microglia in microfluidic connection with dorsal root ganglion cells and challenged with 1 mM ATP to model neuropathic pain, exposure to 10 nM IL6 for 2 hours to model autism, exposure to 30 ng/ml IL1beta and 100 nM TNFalfa for 2 hours to model multiple sclerosis, exposure for 2 hours to 100 µM BzATP of primary microglia cells processed with Mecp2 siRNA to model Rett Syndrome, exposure to 1 mM 3-nitropropionic acid for 24 hours to model HD, exposure to 500 µM kainic acid for 2 hours to model epilepsy, exposure to 100 ng/ml LPS for 24 hours to model meningitis, exposure of primary microglia cells to oxygen glucose deprivation protocol for 2 hours followed by reperfusion in normoxic conditions to model traumatic brain injury, challenge for 30 minutes with 100 µM BzATP of primary microglia cells processed with SOD siRNA to model ALS, challenging of primary hippocampal microglia cells processed with 100 ng/ml LPS for 4 hours and 1 mM ATP for 30 minutes to model depression. Control cells (Untreated) were kept in culture media without triggering stimuli. Following priming, cells were triggered with 100 µM BzATP for 30 minutes under gentle rotation in KRH containing solution. The supernatant, containing shed vesicles, was withdrawn and incubated for 10 min at 4° C. under gentle periodic rotation with streptavidin beads, pre-coated with biotinylated Annexin V. Shed vesicles bound to Annexin-coated beads were then separated from the supernatant by gravity sedimentation at 4° C.

RNA Extraction from Isolated MVs

Total RNA (triplicate of biological samples) were extracted from isolated MVs collected in a RNA preserving solution using Trizol LS Reagent. Total RNA samples were analyzed by capillary electrophoresis on RNA 6000 Nano chip on Agilent Bioanalyzer 2100 Instrument and their integrity was checked through calculation of RNA Integrity Number (RIN). The qualitative control of RNAs obtained from MVs was performed using a RNA 6000 Pico chip on Bioanalyzer 2100 Instrument.

Library Preparation and Sequencing

The sequencing activities were characterized by two main steps: library preparation and their sequencing. The libraries were prepared using TruSeq Small RNA Sample Preparation, a dedicated kit by Illumina, starting from total RNA as input material. The protocol takes advantage of the natural structure common to most known miRNA molecules and selectively enriches specifically in miRNAs. Each library was added with a unique index sequence and checked on Bioanalyzer 2100. Pooled libraries were sequenced on Illumina platform in single read protocol with the production of sequences of 36 bp in length.

Data Analysis

Small RNA sequencing data were processed from raw FASTQ files. Using FastX toolkit, adaptors sequences were clipped from 3' end of each read. Reads with low complexity and with a length less than 16 nucleotides were discarded. Reads passing this QC step were aligned to the hg19 human genome build allowing no mismatches in the seed region and discarding reads with more than 10 multi-mapping hits. Remnants reads were annotated and counted based on genomic annotations. Reads realigning to miRBase were used for differential expression analysis. Normalizations and differential expression tests were performed with Bioconductor Packages.

Results

MicroRNA content of MVs isolated from microglial cells challenged with different neurodegenerative scenarios has been analysed.

Microglial cells obtained from rodent model have been primed to selected inflammatory scenarios. MVs release has then be stimulated with 100 μM BzATP.

Isolated MVs were processed, RNA was isolated and microRNA analysis was carried out. Specific miRNA patterns were evaluated.

Raw data was background-subtracted, Log 2-transformed, and normalized on read per million base. Values for each pathological indication were compared to control, i.e. untreated cells, which were not primed but only exposed to 100 μM BzATP triggering.

MiRNA with ratio/control above 2 were considered upregulated, while MiRNA with ratio/control below 0.5 were considered downregulated.

Table 16 and 17 report the data observed in a AD microglial MVs model, i.e. Abeta-challenged microglial MVs with respect to control. In table 16 are reported the Abeta-upregulated miRNA, in table 17 the Abeta-downregulated miRNA.

TABLE 16

| name | Sequence | RATIO RPM (lib) AD/UT |
|---|---|---|
| miR-125a-5p (SEQ ID 1) | UCCCUGAGACCCUUUAACCUGUGA | 1.51533566 |
| miR-300-3p (SEQ ID 2) | UAUGCAAGGGCAAGCUCUCUUC | 1.521798302 |
| miR-330-3p (SEQ ID 3) | GCAAAGCACAGGGCCUGCAGAGA | 1.530494292 |
| miR-466n-3p (SEQ ID 4) | UAUACAUGAGAGCAUACAUAGA | 1.532714465 |

TABLE 16-continued

| name | Sequence | RATIO RPM (lib) AD/UT |
|---|---|---|
| miR-501-5p (SEQ ID 5) | AAUCCUUUGUCCCUGGGUGAAA | 1.565278253 |
| miR-146a-5p (SEQ ID 6) | UGAGAACUGAAUUCCAUGGGUU | 1.587610021 |
| miR-24-1-5p (SEQ ID 7) | GUGCCUACUGAGCUGAUAUCAGU | 1.730044385 |
| miR-1306-5p (SEQ ID 8) | CACCACCUCCCCUGCAAACGUCC | 1.81131115 |
| miR-744-5p (SEQ ID 9) | UGCGGGGCUAGGGCUAACAGCA | 1.851357934 |
| miR-671-5p (SEQ ID 10) | AGGAAGCCCUGGAGGGGCUGGAG | 2.030987686 |
| miR-134-5p (SEQ ID 11) | UGUGACUGGUUGACCAGAGGGG | 2.06964569 |
| miR-877-5p (SEQ ID 12) | GUAGAGGAGAUGGCGCAGGG | 2.173997574 |

TABLE 17

| name | Sequence | RATIO RPM (lib) AD/UT |
|---|---|---|
| miR-23b-5p (SEQ ID 13) | GGGUUCCUGGCAUGCUGAUUU | 0.368062845 |
| miR-669c-5p (SEQ ID 14) | AUAGUUGUGUGUGGAUGUGUGU | 0.40871633 |
| miR-29b-3p (SEQ ID 15) | UAGCACCAUUUGAAAUCAGUGUU | 0.425022958 |
| miR-195a-5p (SEQ ID 16) | UAGCAGCACAGAAAUAUUGGC | 0.431994357 |
| miR-151-5p (SEQ ID 17) | UCGAGGAGCUCACAGUCUAGU | 0.457756929 |
| miR-374c-3p (SEQ ID 18) | ACUUAGCAGGUUGUAUUAU | 0.480963414 |
| miR-6539 (SEQ ID 19) | GCACAGUGAUGAACUCUGAGGGCU | 0.493012342 |

Table 18 and 19 report the data observed in a PD microglial MVs model, i.e. 6-OHDA-challenged microglial MVs with respect to control. In table 18 are reported the 6-OHDA-upregulated miRNA, in table 19 the 6-OHDA-downregulated miRNA.

TABLE 18

| name | Sequence | RATIO RPM (lib) AD/UT |
|---|---|---|
| miR-16-1-3p (SEQ ID 20) | CCAGUAUUGACUGUGCUGCUGA | 2.014952955 |
| miR-6399 (SEQ ID 21) | UUGCAAUGAUGGUAUUCUGAGG | 2.218515684 |
| miR-6240 (SEQ ID 22) | CCAAAGCAUCGCGAAGGCCCACGGCG | 2.484737566 |
| miR-23a-5p (SEQ ID 23) | GGGGUUCCUGGGGAUGGGAUUU | 2.588268298 |

TABLE 18-continued

| name | Sequence | RATIO RPM (lib) AD/UT |
| --- | --- | --- |
| miR-92a-1-5p (SEQ ID 24) | AGGUUGGGAUUUGUCGCAAUGCU | 2.711519169 |
| miR-219a-1-3p (SEQ ID 25) | AGAGUUGCGUCUGGACGUCCCG | 2.803957322 |
| miR-128-1-5p (SEQ ID 26) | CGGGGCCGUAGCACUGUCUGA | 3.822673178 |

TABLE 19

| name | Sequence | RATIO RPM (lib) AD/UT |
| --- | --- | --- |
| miR-1949 (SEQ ID 27) | CUAUACCAGGAUGUCAGCAUAGUU | 0.246501743 |
| miR-29b-3p (SEQ ID 15) | UAGCACCAUUUGAAAUCAGUGUU | 0.431888556 |
| miR-872-3p (SEQ ID 28) | UGAACUAUUGCAGUAGCCUCCU | 0.454525164 |
| miR-582-3p (SEQ ID 29) | UAACCUGUUGAACAACUGAAC | 0.456753229 |
| miR-338-5p (SEQ ID 30) | AACAAUAUCCUGGUGCUGAGUG | 0.464103281 |
| miR-379-5p (SEQ ID 31) | UGGUAGACUAUGGAACGUAGG | 0.477834147 |
| miR-155-5p (SEQ ID 32) | UUAAUGCUAAUUGUGAUAGGGGU | 0.482096718 |
| miR-450a-5p (SEQ ID 33) | UUUUGCGAUGUGUUCCUAAUAU | 0.482677061 |
| miR-100-5p (SEQ ID 34) | AACCCGUAGAUCCGAACUUGUG | 0.485300306 |
| miR-152-3p (SEQ ID 35) | UCAGUGCAUGACAGAACUUGG | 0.493828596 |
| miR-222-3p (SEQ ID 36) | AGCUACAUCUGGCUACUGGGU | 0.498981358 |

Table 20 and 21 report the data observed in an ischemic microglial MVs model, i.e. oxygen glucose deprived microglial MVs with respect to control. The cells have been exposed to the oxygen glucose deprivation protocol according to Kichev et al. J Biol Chem. 2014 289(13): 9430-9439. In table 20 are reported the oxygen glucose deprived-upregulated miRNA, in table 21 the oxygen glucose deprived-downregulated miRNA.

TABLE 20

| name | Sequence | RATIO RPM (lib) AD/UT |
| --- | --- | --- |
| mir-146b (SEQ ID 54) | UGAGAACUGAAUUCCAUAGGCU | 1.62 |
| mir-188 (SEQ ID 55) | CAUCCCUUGCAUGGUGGAGGG | 1.59 |
| mir-346 (SEQ ID 56) | UGUCUGCCCGAGUGCCUGCCUCU | 2.1 |
| mir-466f-3 (SEQ ID 57) | UACGUGUGUGUGCAUGUGCAUG | 1.6 |
| mir-541 (SEQ ID 58) | AAGGGAUUCUGAUGUUGGUCACACU | 1.49 |
| mir-706 (SEQ ID 59) | AGAGAAACCCUGUCUCAAAAAA | 3.45 |
| mir-712 (SEQ ID 60) | CUCCUUCACCCGGGCGGUACC | 2.45 |
| mir-714 (SEQ ID 61) | CGACGAGGGCCGGUCGGUCGC | 2.36 |
| mir-1224 (SEQ ID 62) | GUGAGGACUGGGGAGGUGGAG | 1.82 |

TABLE 21

| name | Sequence | RATIO RPM (lib) AD/UT |
| --- | --- | --- |
| let-7e (SEQ ID 37) | UGAGGUAGGAGGUUGUAUAGUU | 0.57 |
| mir-18b (SEQ ID 38) | UAAGGUGCAUCUAGUGCUGUUAG | 0.59 |
| mir-19a (SEQ ID 39) | UAGUUUUGCAUAGUUGCACUAC | 0.51 |
| mir-21b (SEQ ID 40) | UAGUUUAUCAGACUGAUAUUCC | 0.65 |
| mir-26b (SEQ ID 41) | UUCAAGUAAUUCAGGAUAGGU | 0.60 |
| mir-29b-1 (SEQ ID 42) | GCUGGUUUCAUAUGGUGGUUUA | 0.64 |
| mir-30c-1 (SEQ ID 43) | UGUAAACAUCCUACACUCUCAGC | 0.57 |
| mir-100 (SEQ ID 44) | AACCCGUAGAUCCGAACUUGUG | 0.6 |
| mir-130a (SEQ ID 45) | GCUCUUUUCACAUUGUGCUACU | 0.63 |
| mir-181c (SEQ ID 46) | AACAUUCAACCUGUCGGUGAGU | 0.25 |
| mir-297a-1 (SEQ ID 47) | AUGUAUGUGUGCAUGUGCAUGU | 0.46 |
| mir-330 (SEQ ID 48) | UCUCUGGGCCUGUGUCUUAGGC | 0.61 |
| mir-342 (SEQ ID 49) | AGGGGUGCUAUCUGUGAUUGAG | 0.55 |
| mir-484 (SEQ ID 50) | UCAGGCUCAGUCCCCUCCCGAU | 0.5 |
| mir-669b (SEQ ID 51) | AGUUUGUGUGCAUGUGCAUGU | 0.31 |
| mir-669e (SEQ ID 52) | UGUCUUGUGUGUGCAUGUUCAU | 0.41 |
| mir-708 (SEQ ID 53) | CAACUAGACUGUGAGCUUCUAG | 0.68 |

The above listed miRNA are mouse miRNA whose sequence is conserved in human. The only exceptions are miR-21b whose human homologue is miR-21 UAGC- UUAUCAGACUGAUGUUGA (SEQ ID 221), mir-297a-1 whose human homologue is mir-297 AUGUAUGUGUG-CAUGUGCAUG (SEQ ID 235) and mir-466f-3, whose human homologue is miR-466 AUACACAUACACG-CAACACACAU (SEQ ID 236).

Table 22 and 23 report the data observed in a Tourette's Syndrome microglial MVs model, i.e. bicuculline exposed microglial MVs with respect to control. Cells have been exposed to 100 μM bicuculline for 2 hours, according to the protocol described in Frick et al. Brain Behav Immun. 2016 57:326-37. In table 22 are reported the bicuculline-upregulated miRNA, in table 23 the bicuculline-downregulated miRNA.

TABLE 22

| name | Sequence | RATIO RPM (lib) AD/UT |
|---|---|---|
| mir-19b-1 (SEQ ID 71) | AGUUUUGCAGGUUUGCAUCCAGC | 1.86 |
| mir-30a (SEQ ID 72) | UGUAAACAUCCUCGACUGGAAG | 5 |
| mir-33 (SEQ ID 73) | GUGCAUUGUAGUUGCAUUGCA | 1.35 |
| mir-99b (SEQ ID 74) | CACCCGUAGAACCGACCUUGCG | 2.38 |
| mir-144 (SEQ ID 75) | GGAUAUCAUCAUAUACUGUAAGU | 1.48 |
| mir-151 (SEQ ID 76) | CUAGACUGAGGCUCCUUGAGG | 1.21 |
| mir-182 (SEQ ID 77) | UUUGGCAAUGGUAGAACUCACACCG | 1.47 |
| mir-223 (SEQ ID 78) | CGUGUAUUUGACAAGCUGAGUUG | 1.60 |
| mir-340 (SEQ ID 79) | UCCGUCUCAGUUACUUUAUAGC | 2.09 |
| mir-374b (SEQ ID 80) | AUAUAAUACAACCUGCUAAGUG | 2.3 |
| mir-1247 (SEQ ID 82) | CGGGAACGUCGAGACUGGAGC | 2.41 |
| mir-432 (SEQ ID 81) | UCUUGGAGUAGAUCAGUGGGCAG | 1.37 |

TABLE 23

| name | Sequence | RATIO RPM (lib) AD/UT |
|---|---|---|
| mir-10b (SEQ ID 63) | UACCCUGUAGAACCGAAUUUGUG | 0.45 |
| mir-22 (SEQ ID 64) | AGUUCUUCAGUGGCAAGCUUUA | 0.29 |
| mir-23b (SEQ ID 65) | GGGUUCCUGGCAUGCUGAUUU | 0.19 |
| mir-132 (SEQ ID 66) | AACCGUGGCUUUCGAUUGUUAC | 0.38 |
| mir-148b (SEQ ID 67) | GAAGUUCUGUUAUACACUCAGGCU | 0.13 |
| mir-154 (SEQ ID 68) | UAGGUUAUCCGUGUUGCCUUCG | 0.37 |

TABLE 23-continued

| name | Sequence | RATIO RPM (lib) AD/UT |
|---|---|---|
| mir-183 (SEQ ID 69) | UAUGGCACUGGUAGAAUUCACU | 0.26 |
| mir-337 (SEQ ID 70) | CGGCGUCAUGCAGGAGUUGAUU | 0.50 |
| mir-1224 (SEQ ID 62) | GUGAGGACUGGGGAGGUGGAG | 0.38 |

The above listed miRNA are mouse miRNA whose sequence is conserved in human. The only exception is miR-151 whose human homologue is miR-151a CUAGACUGAAGCUCCUUGAGG (SEQ ID 237).

Table 24 and 25 report the data observed in a neuropathic pain microglial MVs model, i.e. on microglial MVs obtained from primary microglia in microfluidic connection with dorsal root ganglion cells and challenged with ATP with respect to control. Cells have been challenged with 1 mM ATP for 30 min. according to Yamashita et al. PLoS One. 2016 11:10. In table 24 are reported the challenge-upregulated miRNA, in table 25 the challenge-downregulated miRNA.

TABLE 24

| name | Sequence | RATIO RPM (lib) AD/UT |
|---|---|---|
| mir-126b (SEQ ID 90) | AUUAUUACUCACGGUACGAGUU | 1.75 |
| mir-134 (SEQ ID 91) | UGUGACUGGUUGACCAGAGGGG | 1.64 |
| mir-320 (SEQ ID 92) | GCCUUCUCUUCCCGGUUCUUCC | 2.24 |
| mir-374b (SEQ ID 80) | AUAUAAUACAACCUGCUAAGUG | 2.10 |

TABLE 25

| name | Sequence | RATIO RPM (lib) AD/UT |
|---|---|---|
| let-7a-2 (SEQ ID 83) | UGAGGUAGUAGGUUGUAUAGUU | 0.45 |
| mir-30b (SEQ ID 84) | UGUAAACAUCCUACACUCAGCU | 0.40 |
| mir-103-2 (SEQ ID 85) | AGCUUCUUUACAGUGCUGCCUUG | 0.53 |
| mir-107 (SEQ ID 86) | AGCUUCUUUACAGUGUUGCCUUG | 0.359 |
| mir-142a (SEQ ID 87) | CAUAAAGUAGAAAGCACUACU | 0.162 |
| mir-146a (SEQ ID 88) | UGAGAACUGAAUUCCAUGGGUU | 0.35 |
| mir-151 (SEQ ID 76) | UCGAGGAGCUCACAGUCUAGU | 0.102 |
| mir-374c (SEQ ID 89) | AUAAUACAACCUGCUAAGUG | 0.193 |

The above listed miRNA are mouse miRNA whose sequence is conserved in human. The only exceptions are miR-126b whose human homologue is miR-126

CAUUAUUACUUUUGGUACGCG (SEQ ID 238) and miR-320 whose human homologue is miR-320a AAAAGCUGGGUUGAGAGGGCGA (SEQ ID 239). Table 26 and 27 report the data observed in an autism microglial MVs model, i.e. on IL6 exposed microglial MVs with respect to control. Cells have been exposed to 10 nM IL6 for 2 hours according to Tsilioni et al. Transl Psychiatry. 2015; 5. In table 26 are reported the IL6-upregulated miRNA, in table 27 the IL6-downregulated miRNA.

TABLE 26

| name | Sequence | RATIO RPM (lib) AD/UT |
|---|---|---|
| let-7f-1 (SEQ ID 97) | UGAGGUAGUAGAUUGUAUAGUU | 2.43 |
| mir-19a (SEQ ID 39) | UAGUUUUGCAUAGUUGCACUAC | 3.54 |
| mir-19b-2 (SEQ ID 98) | AGUUUUGCAGAUUUGCAGUUCAGC | 2.19 |
| mir-21b (SEQ ID 40) | UAGUUUAUCAGACUGAUAUUUCC | 4.20 |
| mir-22 (SEQ ID 64) | AGUUCUUCAGUGGCAAGCUUUA | 1.76 |
| mir-137 (SEQ ID 99) | ACGGGUAUUCUUGGGUGGAUAAU | 3.66 |
| mir-142a (SEQ ID 87) | CAUAAAGUAGAAAGCACUACU | 1.67 |
| mir-144 (SEQ ID 75) | GGAUAUCAUCAUAUACUGUAAGU | 5.43 |
| mir-146b (SEQ ID 154) | UGAGAACUGAAUUCCAUAGGCU | 3.26 |
| mir-155 (SEQ ID 100) | UUAAUGCUAAUUGUGAUAGGGGU | 3.92 |
| mir-219b (SEQ ID 101) | AGAUGUCCAGCCACAAUUCUCG | 1.22 |
| mir-338 (SEQ ID 102) | AACAAUAUCCUGGUGCUGAGUG | 3.88 |
| mir-376c (SEQ ID 103) | GUGGAUAUUCCUUCUAUGUUUA | 3.58 |
| mir-379 (SEQ ID 104) | UGGUAGACUAUGGAACGUAGG | 6.86 |
| mir-451a (SEQ ID 105) | AAACCGUUACCAUUACUGAGUU | 3.57 |
| mir-494 (SEQ ID 106) | AGGUUGUCCGUGUUGUCUUCUC | 3.45 |

TABLE 27

| name | Sequence | RATIO RPM (lib) AD/UT |
|---|---|---|
| let-7a-1 (SEQ ID 93) | UGAGGUAGUAGGUUGUAUAGUU | 0.54 |
| mir-34a (SEQ ID 94) | UGGCAGUGUCUUAGCUGGUUGU | 0.55 |
| mir-92b (SEQ ID 95) | AGGGACGGGACGUGGUGCAGUGUU | 0.7 |

TABLE 27-continued

| name | Sequence | RATIO RPM (lib) AD/UT |
|---|---|---|
| mir-211 (SEQ ID 96) | UUCCCUUUGUCAUCCUUUGCCU | 0.34 |

The above listed miRNA are mouse miRNA whose sequence is conserved in human. The only exception is miR-21b whose human homologue is miR-21 UAGCUUAUCAGACUGAUGUUGA (SEQ ID 221).

Table 28 and 29 report the data observed in a MS microglial MVs model, i.e. on IL1beta and TNFalpha exposed microglial MVs with respect to control. Cells have been exposed to 30 ng/mL IL1beta and 100 nM TNFalpha for 2 hours according to Xie et al. Glia, 2016 64:4, 583-602. In table 28 are reported the IL1beta and TNFalpha-upregulated miRNA, in table 29 the IL1beta and TNFalpha-downregulated miRNA.

TABLE 28

| name | Sequence | RATIO RPM (lib) AD/UT |
|---|---|---|
| let-7c-1 (SEQ ID 109) | UGAGGUAGUAGGUUGUAUGGUU | 1.57 |
| mir-20b (SEQ ID 110) | CAAAGUGCUCAUAGUGCAGGUAG | 1.48 |
| mir-142a (SEQ ID 87) | UGUAGUGUUUCCUACUUUAUGGA | 1.54 |
| mir-145a (SEQ ID 111) | AUUCCUGGAAAUACUGUUCUUG | 3.1 |
| mir-186 (SEQ ID 112) | GCCCUAAGGUGAAUUUUUUGGG | 2.89 |
| mir-223 (SEQ ID 78) | UGUCAGUUUGUCAAAUACCCCA | 2.21 |
| mir-664 (SEQ ID 113) | UAUUCAUUUACUCCCCAGCCUA | 5.25 |

TABLE 29

| name | Sequence | RATIO RPM (lib) AD/UT |
|---|---|---|
| mir-17 (SEQ ID 107) | CAAAGUGCUUACAGUGCAGGUAG | 0.35 |
| mir-20a (SEQ ID 108) | UAAAGUGCUUAUAGUGCAGGUAG | 0.19 |

The above listed miRNA are mouse miRNA whose sequence is conserved in human.

Table 30 and 31 report the data observed in a Rett Syndrome microglial MVs model, i.e. on microglial MVs from primary microglia challenged with BzATP processed with Mecp2 siRNA with respect to control. The protocol is according to Lee Way et al. J. Neurosci. 2015, 35 (6) 2516-2529. In table 30 are reported the challenge-upregulated miRNA, in table 31 the challenge-downregulated miRNA.

TABLE 30

| name | Sequence | RATIO RPM (lib) AD/UT |
|---|---|---|
| mir-29b-1 (SEQ ID 42) | UAGCACCAUUUGAAAUCAGUGUU | 3.12 |
| mir-92b (SEQ ID 95) | AGGGACGGGACGUGGUGCAGUGUU | 2.16 |
| mir-199b (SEQ ID 116) | CCCAGUGUUUAGACUACCUGUUC | 2.95 |
| mir-221 (SEQ ID 117) | ACCUGGCAUACAAUGUAGAUUUCUGU | 3.10 |
| mir-296 (SEQ ID 118) | AGGGCCCCCCCUCAAUCCUGU | 1.85 |
| mir-329 (SEQ ID 119) | AGAGGUUUUCUGGGUCUCUGUU | 2.96 |
| mir-382 (SEQ ID 120) | GAAGUUGUUCGUGGUGGAUUCG | 3.51 |

TABLE 31

| name | Sequence | RATIO RPM (lib) AD/UT |
|---|---|---|
| mir-122 (SEQ ID 114) | AAACGCCAUUAUCACACUAA | 0.45 |
| mir-130a (SEQ ID 45) | GCUCUUUUCACAUUGUGCUACU | 0.21 |
| mir-146a (SEQ ID 88) | UGAGAACUGAAUUCCAUGGGUU | 0.22 |
| mir-146b (SEQ ID 54) | UGAGAACUGAAUUCCAUAGGCU | 0.42 |
| mir-342 (SEQ ID 49) | AGGGGUGCUAUCUGUGAUUGAG | 0.42 |

TABLE 31-continued

| name | Sequence | RATIO RPM (lib) AD/UT |
|---|---|---|
| mir-409 (SEQ ID 115) | AGGUUACCCGAGCAACUUUGCAU | 0.25 |

The above listed miRNA are mouse miRNA whose sequence is conserved in human. The only exception is miR-329 whose human homologue is miR-329-5p GAG-GUUUUCUGGGUUUCUGUUUC (SEQ ID 240).

Table 32 and 33 report the data observed in a HD microglial MVs model, i.e. on 3NP exposed microglial MVs with respect to control. Cells have been exposed to 1 mM 3-nitropropionic acid for 24 hours according to Ruy et al. Neurobiol. Dis. 2003:12 121-132. In table 32 are reported the 3NP-upregulated miRNA, in table 33 the 3NP-downregulated miRNA.

TABLE 32

| name | Sequence | RATIO RPM (lib) AD/UT |
|---|---|---|
| mir-34a (SEQ ID 94) | UGGCAGUGUCUUAGCUGGUUGU | 1.73 |
| mir-207 (SEQ ID 129) | GCUUCUCCUGGCUCUCCUCCCUC | 1.72 |
| mir-18a (SEQ ID 130) | UAAGGUGCAUCUAGUGCAGAUAG | 1.97 |
| mir-448 (SEQ ID 131) | UUGCAUAUGUAGGAUGUCCCAU | 2.11 |
| mir-669c (SEQ ID 133) | UACACACACACACACAAGUAAA | 2.16 |

TABLE 33

| name | Sequence | RATIO RPM (lib) AD/UT |
|---|---|---|
| mir-22 (SEQ ID 64) | AGUUCUUCAGUGGCAAGCUUUA | 1.27 |
| mir-29c (SEQ ID 121) | UGACCGAUUUCUCCUGGUGUUC | 0.97 |
| mir-128-1 (SEQ ID 122) | CGGGGCCGUAGCACUGUCUGA | 0.76 |
| mir-132 (SEQ ID 66) | AACCGUGGCUUUCGAUUGUUAC | 0.93 |
| mir-138-1 (SEQ ID 123) | AGCUGGUGUUGUGAAUCAGGCCG | 1.39 |
| mir-218-1 (SEQ ID 124) | UUGUGCUUGAUCUAACCAUGU | 0.94 |
| mir-222 (SEQ ID 125) | UCAGUAGCCAGUGUAGAUCCU | 1.37 |
| mir-344-1 (SEQ ID 126) | UGAUCUAGCCAAAGCCUGACUGU | 1.79 |
| mir-466b-2 (SEQ ID 127) | UGAUGUGUGUGUACAUGUACAU | 0.39 |
| mir-674 (SEQ ID 128) | CACAGCUCCCAUCUCAGAACAA | 0.51 |

The above listed miRNA are mouse miRNA whose sequence is conserved in human. The only exception is miR-466b-2 whose human homologue is miR-466 AUACACAUACACGCAACACACAU (SEQ ID 236).

Table 34 and 35 report the data observed in an epilepsy microglial MVs model, i.e. on kainic acid exposed microglial MVs with respect to control. Cells have been exposed to 500 μM Kainic Acid for 2 hours according to Zhang et al. Curr Neuropharmacol. 20119(2): 388-398. In table 34 are reported the kainic acid-upregulated miRNA, in table 35 the kainic acid-downregulated miRNA.

TABLE 34

| name | Sequence | RATIO RPM (lib) AD/UT |
| --- | --- | --- |
| mir-17 (SEQ ID 107) | CAAAGUGCUUACAGUGCAGGUAG | 2.87 |
| mir-21a (SEQ ID 161) | UAGCUUAUCAGACUGAUGUUGA | 3.56 |
| mir-23b (SEQ ID 65) | GGGUUCCUGGCAUGCUGAUUU | 2.98 |
| mir-24-2 (SEQ ID 162) | GUGCCUACUGAGCUGAAACAGU | 2.05 |
| mir-27b (SEQ ID 163) | AGAGCUUAGCUGAUUGGUGAAC | 3.51 |
| mir-31 (SEQ ID 164) | AGGCAAGAUGCUGGCAUAGCUG | 4.21 |
| mir-34c (SEQ ID 165) | AGGCAGUGUAGUUAGCUGAUUGC | 2.16 |
| mir-129-1 (SEQ ID 166) | CUUUUUGCGGUCUGGGCUUGC | 1.87 |
| mir-140 (SEQ ID 167) | CAGUGGUUUUACCCUAUGGUAG | 2.25 |
| mir-142b (SEQ ID 168) | UCCAUAAAGUAGGAAACACU | 2.64 |
| mir-148a (SEQ ID 169) | AAAGUUCUGAGACACUCCGACU | 3.66 |
| mir-152 (SEQ ID 170) | UAGGUUCUGUGAUACACUCCGACU | 3.11 |
| mir-184 (SEQ ID 171) | CCUUAUCACUUUUCCAGCCAGC | 3.13 |
| mir-199a-1 (SEQ ID 172) | CCCAGUGUUCAGACUACCUGUUC | 3.22 |
| mir-204 (SEQ ID 173) | UUCCCUUUGUCAUCCUAUGCCU | 2.73 |
| mir-212 (SEQ ID 174) | ACCUUGGCUCUAGACUGCUUACU | 3.14 |
| mir-214 (SEQ ID 175) | UGCCUGUCUACACUUGCUGUGC | 1.23 |
| mir-375 (SEQ ID 176) | GCGACGAGCCCCUCGCACAAAC | 2.05 |
| mir-455 (SEQ ID 177) | UAUGUGCCUUUGGACUACAUCG | 2.16 |
| mir-711 (SEQ ID 178) | GGGACCCGGGGAGAGAUGUAAG | 2.68 |
| mir-882 (SEQ ID 179) | AGGAGAGAGUUAGCGCAUUAGU | 1.62 |

TABLE 35

| name | Sequence | RATIO RPM (lib) AD/UT |
| --- | --- | --- |
| let-7d (SEQ ID 134) | AGAGGUAGUAGGUUGCAUAGUU | 0.25 |
| let-7f-1 (SEQ ID 97) | UGAGGUAGUAGAUUGUAUAGUU | 0.34 |
| mir-30a (SEQ ID 72) | UGUAAACAUCCUCGACUGGAAG | 0.23 |
| mir-30e (SEQ ID 135) | UGUAAACAUCCUUGACUGGAAG | 0.2 |
| mir-34b (SEQ ID 136) | AGGCAGUGUAAUUAGCUGAUUGU | 0.15 |
| mir-98 (SEQ ID 137) | CUAUACAACUUACUACUUUCCU | 0.49 |
| mir-124-1 (SEQ ID 138) | CGUGUUCACAGCGGACCUUGAU | 0.28 |
| mir-181a-1 (SEQ ID 139) | AACAUUCAACGCUGUCGGUGAGU | 0.73 |
| mir-181b-1 (SEQ ID 140) | AACAUUCAUUGCUGUCGGUGGGU | 0.88 |
| mir-181d (SEQ ID 141) | AACAUUCAUUGUUGUCGGUGGGU | 0.41 |

TABLE 35-continued

| name | Sequence | RATIO RPM (lib) AD/UT |
|---|---|---|
| mir-185 (SEQ ID 142) | UGGAGAGAAAGGCAGUUCCUGA | 0.22 |
| mir-186 (SEQ ID 112) | CAAAGAAUUCUCCUUUUGGGCU | 0.46 |
| mir-187 (SEQ ID 143) | AGGCUACAACACAGGACCCGGG | 0.18 |
| mir-190a (SEQ ID 144) | UGAUAUGUUUGAUAUAUUAGGU | 0.33 |
| mir-191 (SEQ ID 145) | CAACGGAAUCCCAAAAGCAGCUG | 0.51 |
| mir-301a (SEQ ID 146) | GCUCUGACUUUAUUGCACUACU | 0.33 |
| mir-325 (SEQ ID 147) | CCUAGUAGGUGCUCAGUAAGUGU | 0.25 |
| mir-331 (SEQ ID 148) | CUAGGUAUGGUCCCAGGGAUCC | 0.41 |
| mir-345 (SEQ ID 149) | GCUGACCCCUAGUCCAGUGCUU | 0.31 |
| mir-361 (SEQ ID 150) | UUAUCAGAAUCUCCAGGGGUAC | 0.24 |
| mir-374b (SEQ ID 80) | AUAUAAUACAACCUGCUAAGUG | 0.20 |
| mir-380 (SEQ ID 151) | AUGGUUGACCAUAGAACAUGCG | 0.31 |
| mir-381 (SEQ ID 152) | AGCGAGGUUGCCCUUUGUAUAUU | 0.27 |
| mir-450a-2 (SEQ ID 153) | UUUUGCGAUGUGUUCCUAAUAU | 0.41 |
| mir-497a (SEQ ID 246) | CAGCAGCACACUGUGGUUUGUA | 0.27 |
| mir-497b (SEQ ID 155) | CACCACAGUGUGGUUUGGACGUGG | 0.25 |
| mir-505 (SEQ ID 156) | GGGAGCCAGGAAGUAUUGAUGUU | 0.37 |
| mir-551b (SEQ ID 157) | GAAAUCAAGCUUGGGUGAGACCU | 0.32 |
| mir-664 (SEQ ID 113) | CUGGCUGGGGAAAAUGACUGG | 0.53 |
| mir-742 (SEQ ID 158) | UACUCACAUGGUUGCUAAUCA | 0.36 |
| mir-875 (SEQ ID 159) | UAUACCUCAGUUUUAUCAGGUG | 0.23 |
| mir-935 (SEQ ID 160) | CCCAGUUACCGCUUCCGCUACCGC | 0.47 |

The above listed miRNA are mouse miRNA whose sequence is conserved in human. The only exceptions are miR-497b whose human homologue is miR-497-5p CAGCAGCACACUGUGGUUUGU (SEQ ID 241), miR-664 whose human homologue is miR-664a-5p ACUGGCUAGGGAAAAUGAUUGGAU (SEQ ID 242), miR-21a, human homologue miR-21-5p UAGCUUAUCAGACUGAUGUUGA (SEQ ID 243) and miR-142b whose human homologue is miR-142-5p CAUAAAGUAGAAAGCACUACU (SEQ ID 244).

Table 36 and 37 report the data observed in a meningitis microglial MVs model, i.e. on LPS exposed microglial MVs with respect to control. Cells have been exposed to 100 ng/ml LPS for hours according to Bianco F. et al. J. Immunol. 2005 174, 11:7268-7277. In table 36 are reported the LPS-upregulated miRNA, in table 37 the LPS-downregulated miRNA.

TABLE 36

| name | Sequence | RATIO RPM (lib) AD/UT |
|---|---|---|
| mir-138-1 (SEQ ID 123) | AGCUGGUGUUGUGAAUCAGGCCG | 0.33 |
| mir-192 (SEQ ID 180) | CUGACCUAUGAAUUGACAGCC | 0.31 |
| mir-219a-1 (SEQ ID 181) | UGAUUGUCCAAACGCAAUUCU | 0.21 |
| mir-383 (SEQ ID 182) | AGAUCAGAAGGUGACUGUGGCU | 0.35 |
| mir-466b-3 (SEQ ID 132) | UGAUGUGUGUGUACAUGUACAU | 0.41 |
| mir-542 (SEQ ID 183) | CUCGGGGAUCAUCAUGUCACGA | 0.21 |
| mir-700 (SEQ ID 184) | UAAGGCUCCUUCCUGUGCUUGC | 0.43 |

TABLE 36-continued

| name | Sequence | RATIO RPM (lib) AD/UT |
|---|---|---|
| mir-705 (SEQ ID 185) | GGUGGGAGGUGGGGUGGGCA | 0.31 |
| mir-762 (SEQ ID 186) | GGGGCUGGGGCCGGGACAGAGC | 0.32 |
| mir-1901 (SEQ ID 187) | CCGCUCGUACUCCCGGGGUCC | 0.15 |
| mir-1928 (SEQ ID 188) | AGCUACAUUGCCAGCUC | 0.34 |
| mir-3474 (SEQ ID 189) | CCCUGGGAGGAGACGUGGAUUC | 0.31 |

TABLE 37

| name | Sequence | RATIO RPM (lib) AD/UT |
|---|---|---|
| let-7a-1 (SEQ ID 93) | UGAGGUAGUAGGUUGUAUAGUU | 3.21 |
| mir-10b (SEQ ID 63) | UACCCUGUAGAACCGAAUUUGUG | 3.53 |
| mir-105 (SEQ ID 190) | CCAAGUGCUCAGAUGCUUGUGGU | 2.43 |
| mir-141 (SEQ ID 191) | CAUCUUCCAGUGCAGUGUUGGA | 2.45 |
| mir-155 (SEQ ID 100) | UUAAUGCUAAUUGUGAUAGGGGU | 3.15 |
| mir-191 (SEQ ID 145) | CAACGGAAUCCCAAAAGCAGCUG | 1.87 |
| mir-200c (SEQ ID 192) | CGUCUUACCCAGCAGUGUUUGG | 2.86 |
| mir-201 (SEQ ID 193) | UACUCAGUAAGGCAUUGUUCUU | 3.16 |
| mir-214 (SEQ ID 175) | UGCCUGUCUACACUUGCUGUGC | 1.73 |
| mir-297b (SEQ ID 194) | AUGUAUGUGUGCAUGAACAUGU | 1.78 |
| mir-302c (SEQ ID 195) | GCUUUAACAUGGGGUUACCUGC | 1.65 |
| mir-495 (SEQ ID 196) | GAAGUUGCCCAUGUUAUUUUUCG | 1.67 |
| mir-670 (SEQ ID 197) | AUCCCUGAGUGUAUGUGGUGAA | 2.37 |
| mir-673 (SEQ ID 198) | CUCACAGCUCUGGUCCUUGGAG | 3.24 |
| mir-1934 (SEQ ID 199) | UCUGGUCCCCUGCUUCGUCCUCU | 2.17 |

The above listed miRNA are mouse miRNA whose sequence is conserved in human. The only exception is miR-466b-3 whose human homologue is miR-466 (SEQ ID 236).

Table 38 and 39 report the data observed in a Traumatic Brain injury microglial MVs model, i.e. on microglial MVs from microglia exposed to oxygen glucose deprivation protocol followed by reperfusion in normoxic conditions with respect to control. Primary microglia cells have been exposed to 2 hours oxygen glucose deprivation protocol followed by 2 hours of reperfusion in normoxic conditions, according to Kichev et al. J. Biol. Chem. 2014 289(13): 9430-9439. In table 38 are reported the challenge-upregulated miRNA, in table 39 the challenge-downregulated miRNA.

TABLE 38

| name | Sequence | RATIO RPM (lib) AD/UT |
|---|---|---|
| let-7a-2 (SEQ ID 83) | UGAGGUAGUAGGUUGUAUAGUU | 2.06 |
| let-7b (SEQ ID 203) | UGAGGUAGUAGGUUGUGUGGUU | 1.78 |
| mir-19b-1 (SEQ ID 71) | AGUUUUGCAGGUUUGCAUCCAGC | 2.46 |
| mir-21a (SEQ ID 161) | UAGCUUAUCAGACUGAUGUUGA | 2.35 |
| mir-126b (SEQ ID 90) | AUUAUUACUCACGGUACGAGUU | 3.32 |
| mir-146a (SEQ ID 88) | UGAGAACUGAAUUCCAUGGGUU | 2.56 |
| mir-155 (SEQ ID 100) | UUAAUGCUAAUUGUGAUAGGGGU | 2.54 |
| mir-223 (SEQ ID 78) | CGUGUAUUUGACAAGCUGAGUUG | 3.21 |
| mir-292b (SEQ ID 204) | ACUCAAAACCUGGCGGCACUUUU | 4.32 |

TABLE 39

| name | Sequence | RATIO RPM (lib) AD/UT |
|---|---|---|
| mir-129b (SEQ ID 200) | CAGUGGUUUUACCCUAUGGUAG | 0.43 |
| mir-140 (SEQ ID 167) | CAGUGGUUUUACCCUAUGGUAG | 0.22 |
| mir-185 (SEQ ID 142) | UGGAGAGAAAGGCAGUUCCUGA | 0.27 |
| mir-212 (SEQ ID 174) | ACCUUGGCUCUAGACUGCUUACU | 0.32 |
| mir-328 (SEQ ID 201) | GGGGGCAGGAGGGGCUCAGGG | 0.23 |
| mir-361 (SEQ ID 150) | UUAUCAGAAUCUCCAGGGGUAC | 0.33 |
| mir-487b (SEQ ID 202) | UGGUUAUCCCUGUCCUCUUCG | 0.26 |

The above listed miRNA are mouse miRNA whose sequence is conserved in human. The only exceptions are miR-129b whose human homologue is miR-129-5p CUUUUUGCGGUCUGGGCUUGC (SEQ ID 245), miR-21a whose human homologue is miR-21-5p UAGCUUAUCAGACUGAUGUUGA (SEQ ID 243) and miR-126b whose human homologue is miR-126 CAUUAUUACUUUUGGUACGCG (SEQ ID 238).

Table 40 reports the data observed in a ALS microglial MVs model, i.e. on microglial MVs from microglia challenged with BzATP and processed with SOD siRNA with respect to control. Primary microglia cells processed with SOD siRNA have been challenged with 100 µM BzATP for 30 minutes, according to Brites et al. Front. Cell. Neurosci. 2014 8:117. In table 40 are reported the challenge-downregulated miRNA.

TABLE 40

| name | Sequence | RATIO RPM (lib) AD/UT |
|---|---|---|
| mir-22 (SEQ ID 64) | AGUUCUUCAGUGGCAAGCUUUA | 2.15 |
| mir-125b-2 (SEQ ID 205) | UCCCUGAGACCCUAACUUGUGA | 2.47 |
| mir-146b (SEQ ID 54) | UGAGAACUGAAUUCCAUAGGCU | 3.21 |
| mir-155 (SEQ ID 100) | UUAAUGCUAAUUGUGAUAGGGGU | 1.98 |
| mir-214 (SEQ ID 175) | UGCCUGUCUACACUUGCUGUGC | 3.29 |
| mir-365-1 (SEQ ID 206) | AGGGACUUUUGGGGCAGAUGUG | 2.08 |

The above listed miRNA are mouse miRNA whose sequence is conserved in human.

Tables 41 and 42 report the data observed in a depression microglial MVs model, i.e. on LPS and ATP exposed microglial MVs with respect to control. Cells were processed with 100 mg/ml LPS and 1 mM ATP for 4 hours, according to Brites et al. Front. Cell Neurosci. 2015 8:11. In table 41 are reported the LPS and ATP-upregulated miRNA, in table 42 the LPS and ATP-downregulated miRNA.

TABLE 41

| name | Sequence | RATIO RPM (lib) AD/UT |
|---|---|---|
| mir-132 (SEQ ID 66) | AACCGUGGCUUUCGAUUGUUAC | 2.16 |
| mir-134 (SEQ ID 91) | UGUGACUGGUUGACCAGAGGGG | 2.43 |
| mir-144 (SEQ ID 75) | GGAUAUCAUCAUAUACUGUAAGU | 2.67 |
| mir-182 (SEQ ID 77) | UUUGGCAAUGGUAGAACUCACACCG | 3.61 |
| mir-221 (SEQ ID 117) | ACCUGGCAUACAAUGUAGAUUUCUGU | 4.51 |

TABLE 42

| name | Sequence | RATIO RPM (lib) AD/UT |
|---|---|---|
| mir-34a (SEQ ID 94) | UGGCAGUGUCUUAGCUGGUUGU | 0.15 |
| mir-451a (SEQ ID 105) | AAACCGUUACCAUUACUGAGUU | 0.43 |

The above listed miRNA are mouse miRNA whose sequence is conserved in human.

Finally, Tables 43 and 44 report the data observed in MVs from U87 glioblastoma human cell line, where glioblastoma cells are considered microglial cells, with respect to standard microglia cells. In table 43 are reported the upregulated miRNA, in table 44 the downregulated miRNA.

TABLE 43

| name | Sequence | RATIO RPM (lib) AD/UT |
|---|---|---|
| mir-29b-1 (SEQ ID 42) | GCUGGUUUCAUAUGGUGGUUUAGA | 0.4 |
| mir-32 (SEQ ID 207) | CAAUUUAGUGUGUGUGAUAUUU | 0.1 |
| mir-34a (SEQ ID 94) | UGGCAGUGUCUUAGCUGGUUGU | 0.4 |
| mir-100 (SEQ ID 44) | AACCCGUAGAUCCGAACUUGUG | 0.21 |
| mir-124-1 (SEQ ID 138) | CGUGUUCACAGCGGACCUUGAU | 0.54 |
| mir-125a (SEQ ID 208) | UCCCUGAGACCCUUUAACCUGUGA | 0.28 |
| mir-128-1 (SEQ ID 122) | CGGGGCCGUAGCACUGUCUGAGA | 0.42 |
| mir-128-2 (SEQ ID 209) | GGGGGCCGAUACACUGUACGAGA | 0.92 |
| mir-129-1 (SEQ ID 166) | CUUUUUGCGGUCUGGGCUUGC | 0.45 |
| mir-132 (SEQ ID 66) | ACCGUGGCUUUCGAUUGUUACU | 0.17 |
| mir-135a-1 (SEQ ID 210) | UAUGGCUUUUUAUUCCUAUGUGA | 0.37 |
| mir-137 (SEQ ID 99) | UUAUUGCUUAAGAAUACGCGUAG | 0.31 |
| mir-138-1 (SEQ ID 123) | AGCUGGUGUUGUGAAUCAGGCCG | 0.28 |

TABLE 43-continued

| name | Sequence | RATIO RPM (lib) AD/UT |
|---|---|---|
| mir-139 (SEQ ID 211) | UCUACAGUGCACGUGUCUCCAGU | 0.15 |
| mir-146b (SEQ ID 54) | UGAGAACUGAAUUCCAUAGGCU | 0.41 |
| mir-149 (SEQ ID 212) | UCUGGCUCCGUGUCUUCACUCCC | 0.56 |
| mir-181a-2 (SEQ ID 213) | AACAUUCAACGCUGUCGGUGAGU | 0.21 |
| mir-181b-1 (SEQ ID 140) | AACAUUCAUUGCUGUCGGUGGGU | 0.44 |
| mir-181d (SEQ ID 141) | AACAUUCAUUGUUGUCGGUGGGU | 0.54 |
| mir-184 (SEQ ID 171) | UGGACGGAGAACUGAUAAGGGU | 0.16 |
| mir-185 (SEQ ID 142) | UGGAGAGAAAGGCAGUUCCUGA | 0.35 |
| mir-218-1 (SEQ ID 124) | UUGUGCUUGAUCUAACCAUGU | 0.28 |
| mir-326 (SEQ ID 214) | CCUCUGGGCCCUUCCUCCAG | 0.54 |
| mir-483 (SEQ ID 215) | AAGACGGGAGGAAAGAAGGGAG | 0.23 |
| mir-491 (SEQ ID 216) | AGUGGGGAACCCUUCCAUGAGG | 0.43 |

TABLE 44

| name | Sequence | RATIO RPM (lib) AD/UT |
|---|---|---|
| let-7c (SEQ ID 217) | UGAGGUAGUAGGUUGUAUGGUU | 3.21 |
| mir-9-1 (SEQ ID 218) | UCUUUGGUUAUCUAGCUGUAUGA | 2.51 |
| mir-15b (SEQ ID 219) | UAGCAGCACAUCAUGGUUUACA | 2.54 |
| mir-16-1 (SEQ ID 220) | UAGCAGCACGUAAAUAUUGGCG | 1.46 |
| mir-17 (SEQ ID 107) | CAAAGUGCUUACAGUGCAGGUAG | 2.56 |
| mir-19b-1 (SEQ ID 71) | AGUUUUGCAGGUUUGCAUCCAGC | 2.62 |
| mir-20a (SEQ ID 108) | UAAAGUGCUUAUAGUGCAGGUAG | 2.68 |
| mir-21 (SEQ ID 221) | UAGCUUAUCAGACUGAUGUUGA | 2.07 |
| mir-23a (SEQ ID 222) | GGGGUUCCUGGGGAUGGGAUUU | 1.86 |
| mir-24-1 (SEQ ID 223) | UGCCUACUGAGCUGAUAUCAGU | 3.21 |
| mir-25 (SEQ ID 224) | AGGCGGAGACUUGGGCAAUUG | 2.58 |
| mir-27a (SEQ ID 225) | AGGGCUUAGCUGCUUGUGAGCA | 3.25 |
| mir-30b (SEQ ID 84) | UGUAAACAUCCUACACUCAGCU | 1.56 |
| mir-92a-1 (SEQ ID 226) | AGGUUGGGAUCGGUUGCAAUGCU | 2.48 |
| mir-93 (SEQ ID 227) | CAAAGUGCUGUUCGUGCAGGUAG | 2.67 |
| mir-103a-1 (SEQ ID 228) | AGCAGCAUUGUACAGGGCUAUGA | 2.31 |
| mir-106b (SEQ ID 229) | UAAAGUGCUGACAGUGCAGAU | 2.65 |
| mir-125b-1 (SEQ ID 230) | UCCCUGAGACCCUAACUUGUGA | 1.29 |
| mir-146a (SEQ ID 88) | UGAGAACUGAAUUCCAUGGGUU | 2.19 |
| mir-150 (SEQ ID 231) | UCUCCCAACCCUUGUACCAGUG | 1.38 |
| mir-155 (SEQ ID 100) | UUAAUGCUAAUCGUGAUAGGGGU | 1.53 |
| mir-182 (SEQ ID 77) | UUUGGCAAUGGUAGAACUCACACU | 2.18 |
| mir-183 (SEQ ID 69) | UAUGGCACUGGUAGAAUUCACU | 2.07 |

TABLE 44-continued

| name | Sequence | RATIO RPM (lib) AD/UT |
|---|---|---|
| mir-210 (SEQ ID 232) | AGCCCCUGCCCACCGCACACUG | 3.51 |
| mir-221 (SEQ ID 117) | ACCUGGCAUACAAUGUAGAUUU | 2.47 |
| mir-223 (SEQ ID 78) | CGUGUAUUUGACAAGCUGAGUU | 3.15 |
| mir-328 (SEQ ID 201) | GGGGGGGCAGGAGGGGCUCAGGG | 2.51 |
| mir-381 (SEQ ID 152) | AGCGAGGUUGCCCUUUGUAUAU | 4.21 |
| mir-451a (SEQ ID 105) | AAACCGUUACCAUUACUGAGUU | 2.31 |
| mir-718 (SEQ ID 233) | CUUCCGCCCCGCCGGGCGUCG | 4.32 |
| mir-335 (SEQ ID 234) | UCAAGAGCAAUAACGAAAAAUGU | 5.24 |

The invention claimed is:

1. A method for the in vitro diagnosis of Parkinson's Disease (PD) in an individual, wherein the method comprises the steps:
   a) isolating microglial microvesicles (MVs) from biological fluids obtained from an individual;
   b) collecting the miRNA contained in said MVs;
   c) determining the expression profile of a predetermined set of miRNA, defining a microglial MVs miRNA pattern;
   d) comparing said expression profile to one or several reference expression profiles obtained from at least one healthy individual, or an individual not having Parkinson's Disease (PD); and,
   e) treating said individual with a suitable therapy based on the diagnosis of said individual;
   whereby a difference between said determined expression profile and said one or several reference expression profiles is indicative of Parkinson's Disease (PD);
   whereby said microglial MVs miRNA pattern, with respect to said reference pattern, is characterised as follows:
   downregulated miRNA: miR-100-5p (SEQ ID 34), miR-152-3p (SEQ ID 35), miR-155-5p (SEQ ID 32), miR-1949 (SEQ ID 27), miR-501-5p (SEQ ID 5), miR-6399 (SEQ ID 21), miR-872-3p (SEQ ID 28);
   upregulated miRNA: miR-128-1-5p (SEQ ID 26), miR-16-1-3p (SEQ ID 20), miR-219a-1-3p (SEQ ID 25), miR-222-3p (SEQ ID 36), miR-23a-5p (SEQ ID 23), miR-338-5p (SEQ ID 30), miR-379-5p (SEQ ID 31), miR-450a-5p (SEQ ID 33), miR-582-3p (SEQ ID 29), miR-6240 (SEQ ID 22), miR-92a-1-5p (SEQ ID 24).

2. The method according to claim 1, wherein said microglial MVs miRNA pattern, with respect to said reference pattern, is characterised as follows:
   downregulated miRNA: miR-100-5p (SEQ ID 34), miR-152-3p (SEQ ID 35), miR-1949 (SEQ ID 27), miR-501-5p (SEQ ID 5); and,
   upregulated miRNA: miR-128-1-5p (SEQ ID 26), miR-16-1-3p (SEQ ID 20), miR-219a-1-3p (SEQ ID 25), miR-222-3p (SEQ ID 36), miR-23a-5p (SEQ ID 23), miR-338-5p (SEQ ID 30), miR-379-5p (SEQ ID 31), miR-450a-5p (SEQ ID 33), miR-582-3p (SEQ ID 29), miR-92a-1-5p (SEQ ID 24).

* * * * *